(12) United States Patent
Roh et al.

(10) Patent No.: US 11,864,854 B2
(45) Date of Patent: Jan. 9, 2024

(54) ROBOTIC SURGERY SYSTEM WITH TOOL EDGE SENSORS FOR EDGE COMPUTING

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/901,675

(22) Filed: Sep. 1, 2022

(65) Prior Publication Data

US 2023/0338099 A1    Oct. 26, 2023

Related U.S. Application Data

(63) Continuation of application No. 17/729,959, filed on Apr. 26, 2022, now Pat. No. 11,464,590.

(51) Int. Cl.
*A61B 34/35* (2016.01)
*G16H 40/67* (2018.01)
*A61B 17/16* (2006.01)
*A61B 17/00* (2006.01)

(52) U.S. Cl.
CPC .......... *A61B 34/35* (2016.02); *A61B 17/1626* (2013.01); *G16H 40/67* (2018.01); *A61B 2017/00075* (2013.01); *A61B 2017/00119* (2013.01); *A61B 2017/00203* (2013.01); *A61B 2017/00221* (2013.01)

(58) Field of Classification Search
CPC ..... A61B 34/35; A61B 17/1626; G16H 40/67
See application file for complete search history.

(56) References Cited

U.S. PATENT DOCUMENTS

| 11,464,590 | B1 | 10/2022 | Roh et al. | |
| 2019/0201136 | A1* | 7/2019 | Shelton, IV | G16H 50/20 |
| 2019/0206562 | A1* | 7/2019 | Shelton, IV | A61B 17/0206 |
| 2020/0078119 | A1* | 3/2020 | Henderson | A61B 50/13 |
| 2020/0289223 | A1* | 9/2020 | Denlinger | A61B 34/77 |

* cited by examiner

*Primary Examiner* — Nathaniel C Chukwurah
(74) *Attorney, Agent, or Firm* — Perkins Coie LLP

(57) ABSTRACT

Methods, apparatuses, and systems for edge computing in surgical robotics is provided. The system comprises a surgical robot communicatively coupled to a 3rd party operating room equipment system over a cloud network. The surgical robot includes an operating room hardware configured to perform a surgical procedure on a patient. A memory is communicatively coupled to operating room hardware and user interface, and the memory comprises an equipment database and a threshold database to store parameters related to the operating room hardware. A processor, coupled to the operating room hardware via the network interface, is configured to establish a connection between the surgical robot and the 3rd party operating room equipment system, and monitor events being performed by the operating room and then store the monitored data within the threshold database. The threshold database stores trigger values for each piece of equipment for taking actions, based on data collected by sensors.

20 Claims, 14 Drawing Sheets

EQUIPMENT DATABASE (OPERATING ROOM HARDWARE)

| Surgical Equipment | Surgery Required | Temperature of Equipment (°C) | Temperature of Tissue (°C) | Force Applied (N) | Deformation (mm) | Orientation (degrees) | Pressure (bar) |
|---|---|---|---|---|---|---|---|
| Drill | Bone Replacement | 25-33 | 36.5 | 10-12 | -- | 2 (vertical) / 5 (horizontal) | -- |
| Endoscope | Stomach Diagnostics | 26-32 | 35.5 | 9-12 | -- | 7 (vertical) / 6 (horizontal) | -- |
| Forceps | Abdomen Surgery | 25-30 | 35.6 | 10 | -- | 8 (vertical) / 9 (horizontal) | -- |
| Stapler | Securing Tissues | 25-30 | 36.5 | 10-12 | 2-3 | 1 (vertical) / 7 (horizontal) | -- |
| Insufflator | Abdominal Surgery | 25-33 | 35.5 | 10-11 | -- | 5 (vertical) / 2 (horizontal) | 3.0-3.6 / 1.0-1.4 |

*FIG. 7*

THRESHOLD DATABASE (OPERATING ROOM HARDWARE)

| Surgical Equipment | Surgery Required | Operating Temperature of Equipment (°C) | Operating Temperature of Tissue (°C) | Force Applied (N) | Pressure (bar) | Max/Min Temperature Threshold | Trigger Temperature | Action |
|---|---|---|---|---|---|---|---|---|
| Drill | Bone Replacement | 30 | 36.5 | 10 | -- | 30 / 40 | 37 | Slow drill when trigger temperature reached and provide notification to surgeon |
| Endoscope | Stomach Diagnostics | 30 | 36.5 | 10 | -- | 35 / 45 | 38 | Stop drill when maximum temperature reached and provide notification to surgeon |
| Forceps | Abdomen Surgery | 30 | 36.5 | 10 | -- | 32 / 42 | 38 | Slow drill when trigger temperature reached and provide notification to surgeon |
| Stapler | Securing Tissues | 30 | 36.5 | 10 | 2 | 34 / 43 | 37 | Stop drill when maximum temperature reached and provide notification to surgeon |
| Insufflator | Abdominal Surgery | 30 | 36.5 | -- | 3.5 | 30 / 40 | 38 | Slow drill when trigger temperature reached and provide notification to surgeon |

ROBOTIC SURGERY SYSTEM WITH TOOL EDGE SENSORS FOR EDGE COMPUTING

CROSS-REFERENCE TO RELATED APPLICATION

This application is a continuation of U.S. patent application Ser. No. 17/729,959, filed Apr. 26, 2022, which is incorporated herein by reference in its entirety.

TECHNICAL FIELD

The present disclosure is generally related to an apparatus, a system, and a method for tool edge computing sensors and more particularly related to an apparatus for monitoring a surgical tool.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and among the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 7 illustrates an equipment database for the system, according to an embodiment.

FIG. 8 illustrates a threshold database for the system, according to an embodiment.

DETAILED DESCRIPTION

Figure 1:
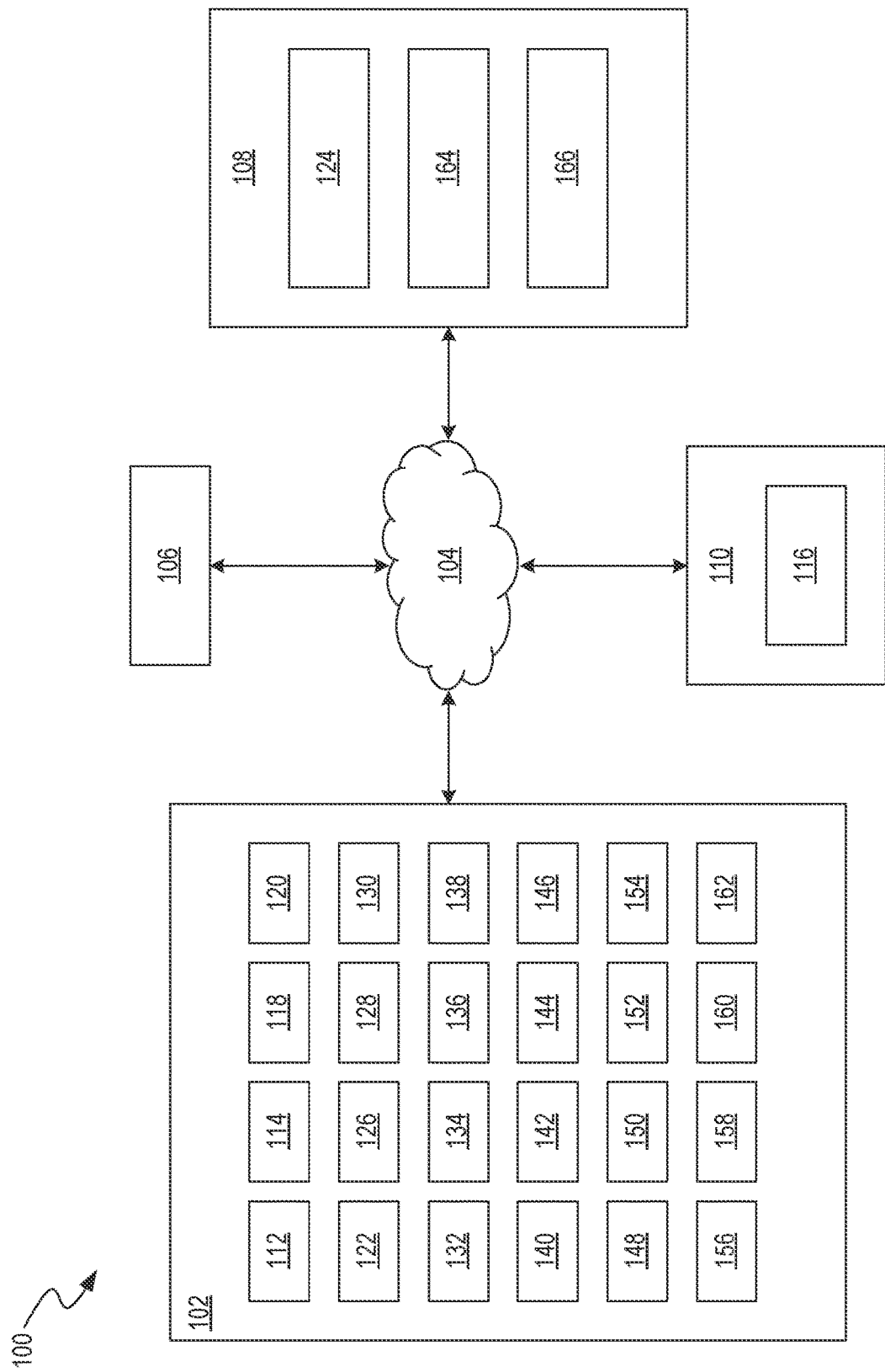
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "602") can implement components, operations, or structures (e.g., "602a") described as a single instance. Further, plural instances (e.g., "602") refer collectively to a set of components, operations, or structures (e.g., "602a") described as a single instance. The description of a single component (e.g., "602a") applies equally to a like-numbered component (e.g., "602b") unless indicated otherwise. These and other aspects, features, and implementations can be expressed as methods, apparatus, systems, components, program products, means or steps for performing a function, and in other ways. These and other aspects, features, and implementations will become apparent from the following descriptions, including the claims.

Surgical tools are used to perform precise actions. Suboptimal functioning, such as lower than needed rotational speed, can result in complications during a surgical procedure. Many surgical tools exist and some surgical tools, such as drills are used in different procedures, despite otherwise being identical. Such tools need to be customized for each procedure. For example, a drill can have a higher maximum rotational speed for one procedure, while another otherwise identical drill can have a lower rotational speed to ensure the patient is not harmed or other surgical implements such as an implant is not damaged during the procedure. Additional tools increase cost and the complexity of tool maintenance and inventory management. Traditionally, a surgeon is trained in the use of a tool prior to its use. However, surgeons still have questions, particularly when using a new tool. Further, a surgeon may wish to have a greater amount of control over their tool, such as limiting the amount of power or the rotational speed of a tool to ensure that harm is not done to the patient.

Robotic telesurgery system has a potential to provide healthcare surgical services to patients at remote locations using wireless communication. The robotic telesurgery system can work as a master-slave system and the possibility for using the master-slave system to perform robotic telesurgery procedures has been recognized in 2001, when first robotic telesurgery was conducted on a patient in Strasbourg, France, by Professor Jacques Marescaux. The telesurgery system has led to the foundation of the globalization of surgical procedures. In the robotic telesurgery system, a surgeon at a master site performed surgery by guiding a surgical robot at the surgical site. The surgeon at the master site controlled the surgery by sending various control commands to the surgical site through a human system interface, which mainly comprised of haptic devices, headphones, and video consoles for audio-video feedback. The robotic telesurgery system has made a significant societal impact as it fulfilled the shortage of surgeons and also eliminated geographical barriers to provide timely and high-quality surgical intervention. The robotic telesurgery system further has prevented complications, financial burden, and often risky long-distance travel. Further, the telesurgery system has provided benefits not only to patients but also to the surgeons by ensuring their safety.

Numerous technological advancements like edge computing, in telesurgery systems have occurred to improve accuracy and reliability. Currently, edge computing is being used to bring processing of data close to the surgical site and overcome the disadvantages associated with latency time. Using the edge computing at the surgical site enables operation room equipment to operate continuously, in critical conditions, even with a minor delay from the remote surgeon. The use of the edge computing also removes any limitation by bandwidth or latency of connection to a centralized processor. In some embodiments, a system can analyze one or more network-related parameters (e.g., latency times, predicted latency times, data rates, etc.) to determine one or more computing steps for edge computing. For example, a robotic surgery system connected to a telesurgery system can predict when latency times may affect a surgical procedure. The robotic surgery system can then perform edge computing to compensate for network-related parameters. The robotic surgery system can identify local computing resources (e.g., surgical robots, computing devices, such as tools, sensors, etc.), or surgical room components configured to perform edge-computing surgical monitoring. The robotic surgery system can locally monitor, plan, perform, and/or complete surgical steps. In some embodiments, the robotic surgical system can be configured to identify one or more adverse events, such as excess latency times (e.g., latency times that exceed a threshold latency time), communication channel failures, network communication failures, or other events that can affect surgery.

The robotic system can autonomously identify the events, and in response to the identification, perform one or more corrective actions based, at least in part, edge computing, tool monitoring, etc. This allows the robotic surgery system to automatically perform local processes as needed. In some embodiments, when an adverse event is detected, the robotic surgery system can automatically determine one or more edge computing processes to compensate for the adverse event. For example, in response to data rate decreases, the robotic surgery system can locally compensate for such data rate decreases using edge computing. The robotic surgery system can monitor tools, including 3rd party tools without communicating with the tools.

Surgical procedures can involve remote computing, local computing, or combinations thereof. In some embodiments, the robotic surgery system can determine a maximum or threshold time period for performing a task. The robotic surgery system can then predict an expected period of time for performing the task using network communications and remote processing. In response to the expected period time exceeding the maximum time period, the surgery system can then perform the task using local resources (e.g., only local resources or a combination of remote and local resources). For example, robotic surgery system can use edge computing (or edge monitoring) performed by surgical room equipment to complete the task within the maximum or threshold time period. In some embodiments, the maximum or threshold time period can be, for example, obtained from a surgical plan, inputted by a physician, inputted by surgical team, calculated by the robotic surgery system using machine learning engines trained using training sets with time periods for tasks and associate outcomes, or combinations thereof. The tasks can include, without limitation, image processing, simulations, tissue analysis, patient monitoring, or other actions disclosed herein. For example, the robotic surgery system can analyze images to detect one or more edges (e.g., detect edges of, for example, tissue, anatomical features, margins, instruments, tool features, etc.). Edge detection is a mathematical tool for identifying edges, curves, and other features of interest in a digital image captured by an image processing technique. The purpose of detecting sharp changes in image brightness can be to capture important events and changes in the properties of an object being captured. Edge detection has multiple applications in different fields such as, but not limited to, computer processing, medical applications such as eye surgery, oncology surgery, etc. Oncology surgery can be performed with advanced robotics having a robot arm and an end effector to perform surgery such as removing cancer cells from a tumor in a patient. Sometimes, removing cancer cells leaves behind residual cancer. Residual cancer, which refers to cancer cells left behind after an initial resection surgery, can lead to local recurrence, increased rates of metastasis, and poorer outcomes. Currently, there is a high rate of secondary surgeries because cancer cells are found at the margins of the resected mass during a post-operative pathological analysis of the tumor. For example, 50% of breast-conserving lumpectomies, 35% of limb-sparing sarcoma surgeries, and 37% of radical prostatectomies fail to completely remove cancer cells during the initial surgery. In many cases, effective and total resection of cancers in organs is further complicated because essential adjacent structures need to be spared. For example, brain surgeries or other surgeries where important nerves or blood vessels are nearby. In some embodiments, robotic surgery systems can perform one or more edge computing or monitoring steps to, for example, detect edges, analyze tissue, or other sensing independent of network connection speeds, latency times, monitor surgical sites, monitor surgical tools and equipment, or the like.

In order to reduce the time, effort, and/or improve outcomes, methods and systems have been developed. One such system was the application of lasers with precisely modulated laser frequency, time of exposure, and intensity or amplitude of laser. The laser surgery is mainly used to vaporize a specific portion of tissue from a patient's body using the precisely modulated laser frequency as different frequencies of light have different effects on objects such as tissues. Further, laser surgery is used to on internal and external tissues of the patient, due to its capability to cut through tissues. For example, ablating tissues, removing cancerous cells, treating skin, eyes, etc. Further, with the introduction of automated surgery, the use of computer-modulated lasers has become more frequent and the doctors can perform surgeries remotely using robot arms. Thus, a system is required that can provide critical real-time assistance to the surgeon, during a surgical procedure. In some embodiments, systems disclosed herein can provide real-time assistance by performing edge computing of acquired data. Edge computing can be used to, for example, control laser surgery systems, robotic arms, and other laser-based steps, including ablation steps. Captured image data can be locally analyzed. In some embodiments, laser end effectors can be programmed to perform edge computing used to complete one or more surgical laser-based steps. The robotic surgery system can control the edge computing performed by the laser end effectors.

At least some of the embodiments disclosed herein describe methods, apparatuses, and systems for maintaining and controlling surgical systems and tools. In some embodiments, for each surgical tool, a surgeon can give verbal commands, which can result in feedback provided by a synthesized voice or the execution of an action as instructed by the verbal command. The tools are monitored during use to ensure the tools remain within their operating parameters. The system alerts the surgeon should the tools approach their operational limitations. In some embodiments, a robotic surgical apparatus performing the surgical steps can locally analyze output from sensors, including third party tool sensors. The robotic surgical apparatus can be communicatively coupled to the sensors via a wired connection, wireless connection (e.g., via a local wireless network, mesh network, etc.), optical connection, or the like. The robotic apparatus can then control the tools based on the analysis. In some embodiments, the robotic apparatus can discover surgical tool via a wireless connection, wired connection, etc. The robotic apparatus can receive data for newly discovered tools. The data can include, without limitation, software, communication protocols, authorization data, operational data, or combinations thereof. The robotic apparatus can perform surgical steps using the received data and can retrieve additional data as needed.

In some embodiments, tools that perform surgical steps can also analyze their collected data using one or more edge computing processes. This allows each tool to self-monitor performance to provide for monitoring redundancy independent of the system's ability to communicate with other systems or networks. In some embodiments, the tools can communicate, via one or more wired or wireless connections, with one another for distributed processing. Processing steps can be performed by tools based on available resources of each tool to, for example, reduce processing times, manage computational resources, and to manage communication channels.

The advantages and benefits of the methods, systems, and apparatus disclosed herein include compatibility with best practice guidelines for performing surgery in an operating room, e.g., from regulatory bodies and professional standards organizations such as the Association for Surgical Technologists. The robotic surgical system disclosed herein can include surgical tools maintained to be in an immediate state of readiness. Further, the embodiments disclosed provide methods for performing maintenance and tracking such that a tool remains operational at all times. The disclosed methods provide maintenance according to the manufacturer's instructions and/or maintenance based on the passage of time or tool usage. As such, the disclosed systems provide methods of interacting with and controlling the operational parameters of a surgical tool. In addition, the embodiments disclosed provide that maintenance is performed routinely and prior to use during a surgical procedure. Thus, a tool's reliability increases. Enabling a surgeon to interact with and adjust the configuration of a tool during a procedure—when their hands may be unavailable to interface with the tool—affords the surgeon increased control over the tool. Moreover, the embodiments reduce manual interactions with a physical interface on a tool that can cause the tool to move in a manner which could harm the patient. The resulting tool is more efficient, can be operated more safely, and can provide increased precision.

The robotic surgery technologies disclosed further offer improved enhancements to medical or surgical processes through improved precision, stability, and dexterity. The disclosed methods relieve medical personnel from routine tasks and make medical procedures safer and less costly for patients. The embodiments disclosed enable more accurate surgery to be performed in more minute locations on or within the human body. The embodiments also address the use of dangerous substances. The adoption of robotic systems, according to the embodiments disclosed herein, provides several additional benefits, including efficiency and speed improvements, lower costs, and higher accuracy. The equipment tracking system integrated into the disclosed embodiments offers flexibility and other advantages, such as requiring no line-of-sight, reading multiple radio frequency identification (RFID) objects at once, and scanning at a distance. The advantages offered by the surgical tower according to the embodiments disclosed herein are smaller incisions, less pain, lower risk of infection, shorter hospital stays, quicker recovery time, less scarring, and reduced blood loss. The advantages of the convolutional neural network (CNN) used for machine learning (ML) in the disclosed embodiments include the obviation of feature extraction and the use of shared weight in convolutional layers, which means that the same filter (weights bank) is used for each node in the layer; this both reduces memory footprint and improves performance.

In some embodiments, systems for edge computing or monitoring include a surgical robot communicatively coupled to a 3rd party operating room equipment system over a cloud network. The surgical robot includes an operating room hardware configured to perform a surgical procedure on a patient. The surgical robot can be communicatively coupled to operating room hardware and user interface. The surgical robot can access an equipment database and a threshold database to manage parameters related to the operating room hardware. The system can establish a connection between the surgical robot and the 3rd party operating room equipment system, and monitor events being performed by the operating room and then store the monitored data within the threshold database. The threshold database can include values (e.g., threshold values, trigger values, etc.) for each piece of equipment.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or outpatient surgery center.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiological parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end tidal CO2 monitor or capnography monitor used for measurement of the level of carbon dioxide that is released at the end of an exhaled breath (referred to as end tidal carbon dioxide, ETCO2). An end tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end tidal CO2 monitor can be configured as side stream (diverting) or mainstream (non-diverting). A diverting end tidal CO2 monitor transports a portion of a patient's respired gases from the sampling site to the end tidal CO2 monitor while a non-diverting end tidal CO2 monitor does not transport gas away. Also, measurement by the end tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in artery, used in the operating room 102) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate—the rate at which breathing occurs—and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding the surgeon during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation. Spontaneous EMG is recorded by the insertion of a needle electrode. Triggered EMG refers to the recording of myoelectric signals during stimulation of a target site such as a pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgeon or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. The doctor moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgeon makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals across long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles, which allow the surgeon to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 128 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels that are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument can 130 consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools thereby minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used can be brain/spinal cord anomalies, tumors in the body, breast cancer screening, joint injuries, uterine/pelvic pain detection, or heart problems. For the creation of the image by an MRI instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI is more widely suitable for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"— of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgeons in the placement of specialized surgical instruments and implants. The patient images are taken to guide the physician before or during the medical procedure. The stereotactic navigation system 138 includes a camera having infrared sensors to determine the location of the tip of the probe being used in the surgical procedure. This information is sent in real-time so that the surgeons have a clear image of the precise location where they are working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (02), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table that is designed for use in spinal surgeries and can be used in a variety of spinal procedures in supine, prone, or lateral positions in a safe manner. Two peculiar features of the Jackson table 144 are the absence of central table support and an ability to rotate the table through 180 degrees. The Jackson table 144 is supported at both ends, which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors that can contribute to poor quality in the environment of the operating room 102 are temperature, ventilation, and humidity, and those conditions can lead to profound effects on the health and work productivity of people in the operating room 102. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter (HEPA filter). A HEPA filter protects a patient from infection and contamination using a filter, which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, or a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by doctors and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries are performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patients' medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

Figure 2:
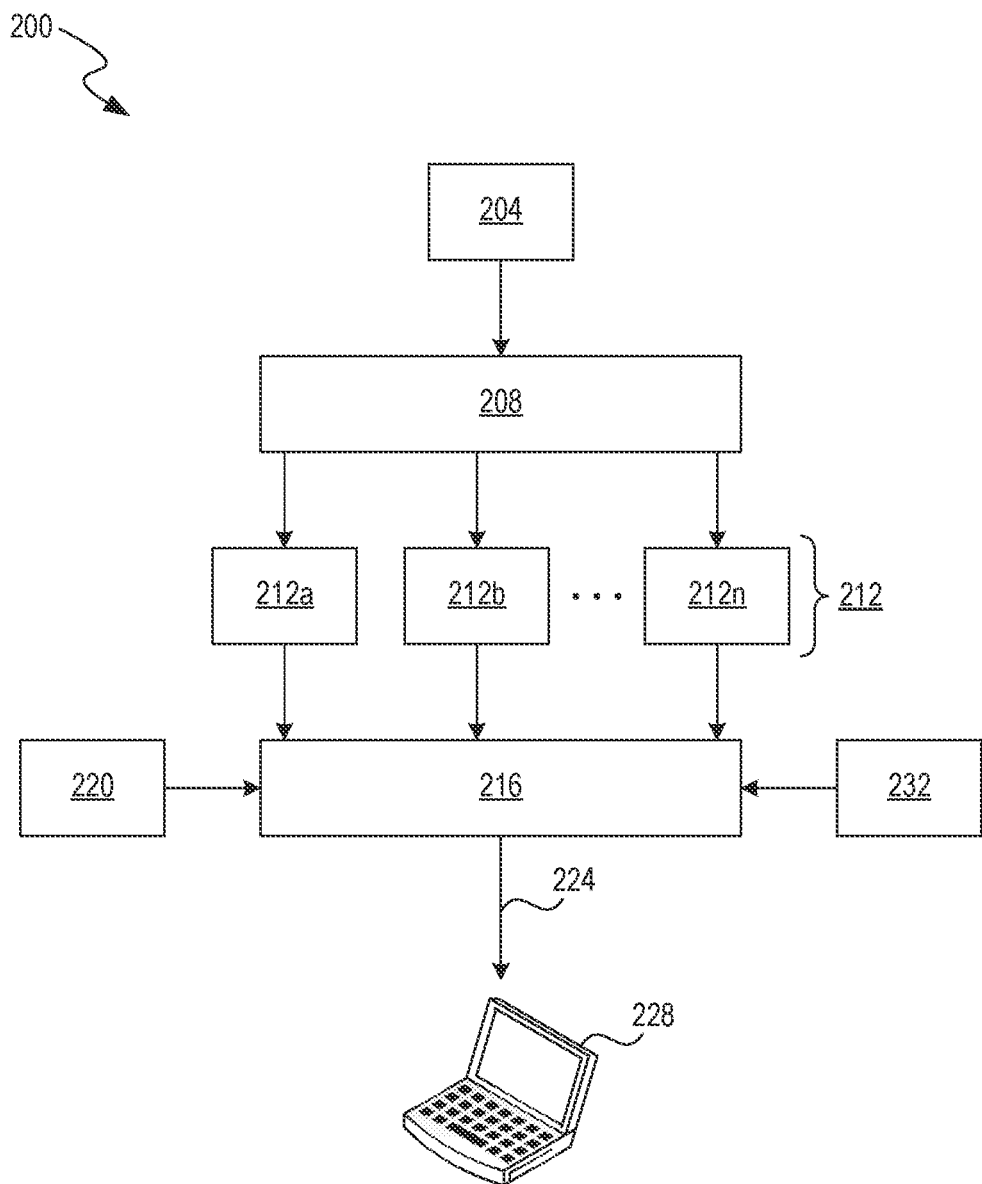
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., features 212a, 212b, . . . , 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place.

Figure 3:
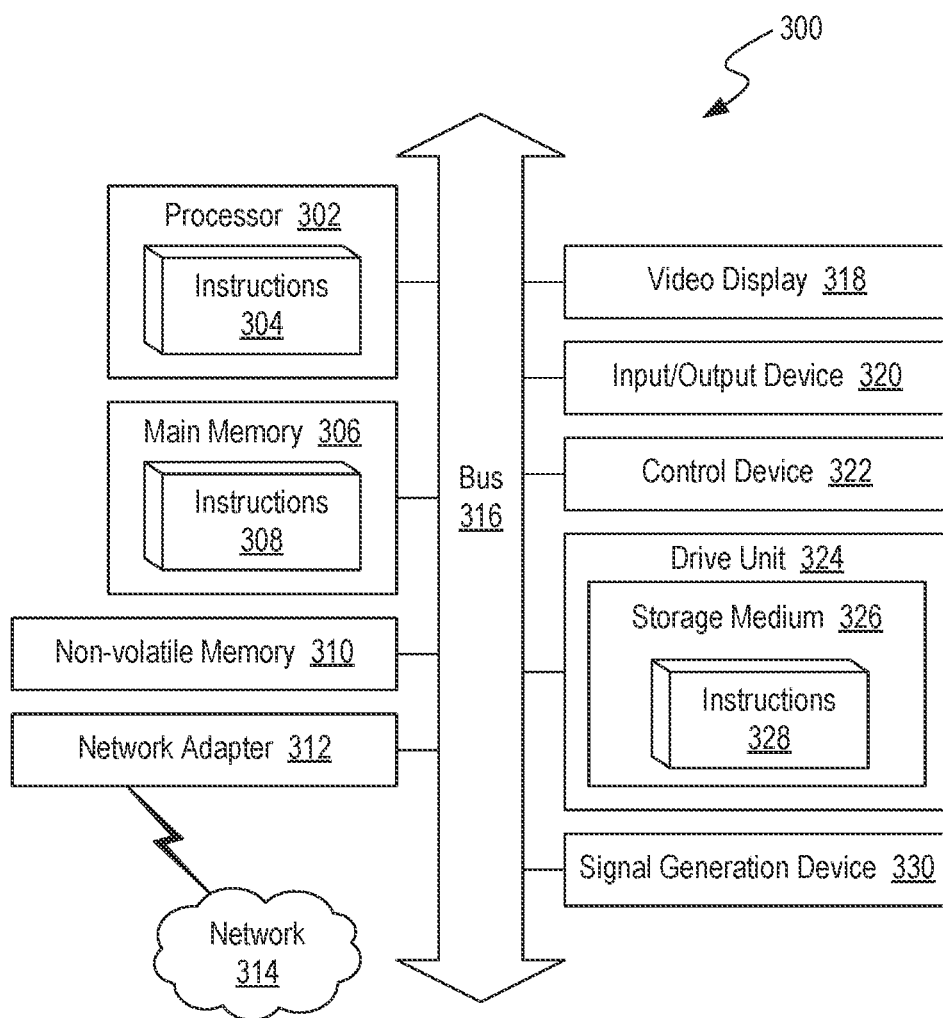
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
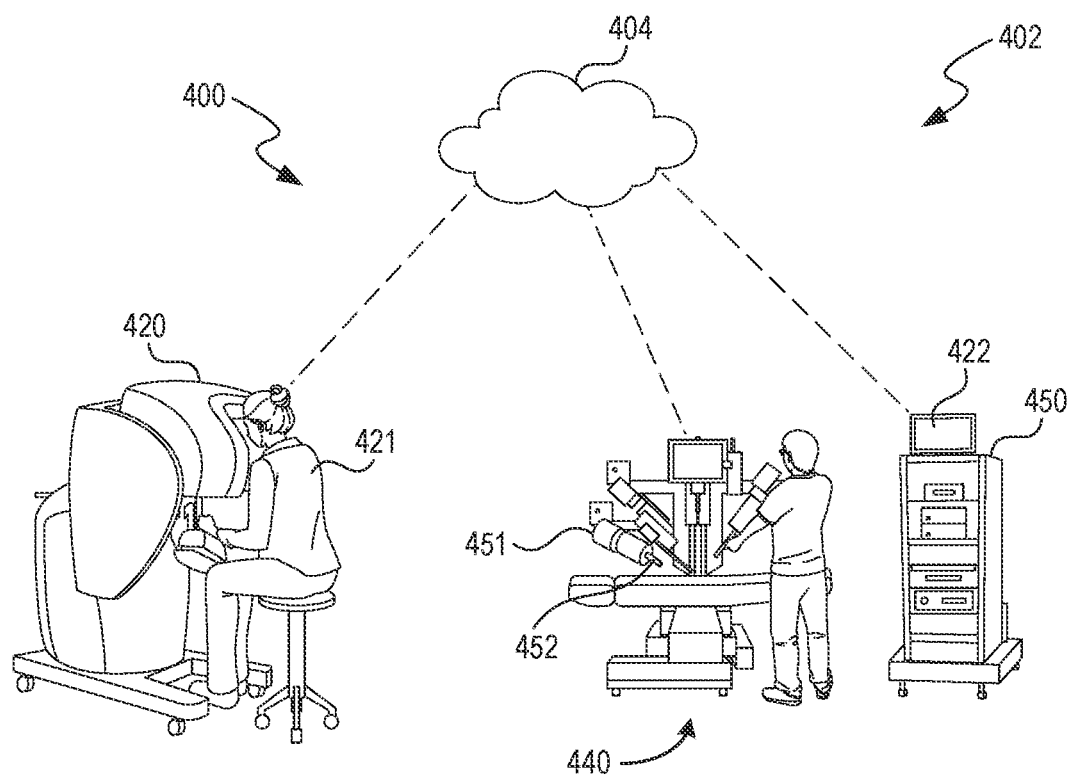
FIG. 4A is a block diagram illustrating an example robotic surgical system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1).

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc. or other features disclosed herein to perform surgical step(s) or procedures or implement steps of processes discussed herein.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed, and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

Figure 4B:
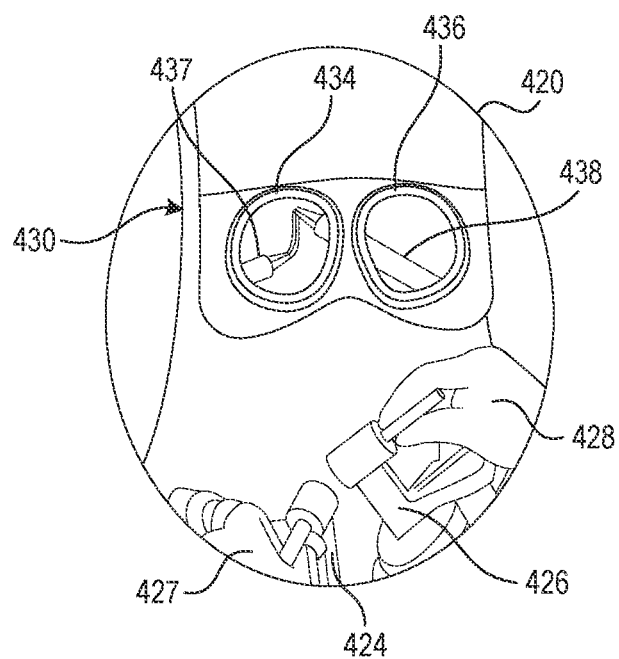
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. In some embodiments, one or both instruments 437, 438 can provide sensor data used by the robotic surgical system 400. In some embodiments, the surgical instrument 437 can include a tool edge sensor for, for example, determining, analyzing, etc. applied pressures, forces, temperatures, or other data. The instrument 437 or other components of the robotic surgical system 400 can perform edge computing or monitoring with the data to determine whether the instrument 437 is operating within a desired range. In some embodiments, the sensor data can be calculated (e.g., determine a value), averaged, and compared to acceptable thresholds. If the calculated value (e.g., average of the data, average of set sampled data, etc.) is not within an acceptable range, a notification can be provided to the operator or user 421 of FIG. 4A. Additionally, or alternatively, the output from the instrument 437 can be displayed via display 422 of FIG. 4A. In some embodiments, the instrument 438 of FIG. 4B includes one or more imaging devices to determine instrument position, visualize the surgical area, identify tissues, or other features of interest associated with the surgical procedure.

Referring to FIG. 4B, the user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452.

In an autonomous mode, the surgical robot 440 can autonomously perform steps under the control of the data system 450. The robotic surgical system 400 can be preprogrammed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include physician input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds. The adverse surgical events can be identified using a machine learning model trained using, for example, prior patient data, training sets (e.g., tool data), etc.

In some embodiments, the robotic surgical system 400 determines whether a detected event (e.g., operational parameters outside a target range or exceeding a threshold, etc.) is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like.

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre-, or post-operative virtual simulations, simulations using models, etc.) can be generated and collected.

The surgical robot 440 can include robotic arms 451 (one identified) with integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein.

The robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, California. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modified, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operative or intraoperatively.

Embodiments can provide a means for mapping the surgical path for neurosurgery procedures that minimize damage through artificial intelligence mapping. The software for artificial intelligence is trained to track the least destructive pathway. The physician can make an initial incision based on a laser marking on the skin that illuminates the optimal site. Next, a robot can make a small hole and insert surgical equipment (e.g., guide wires, cannulas, etc.)

that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

Figure 5:
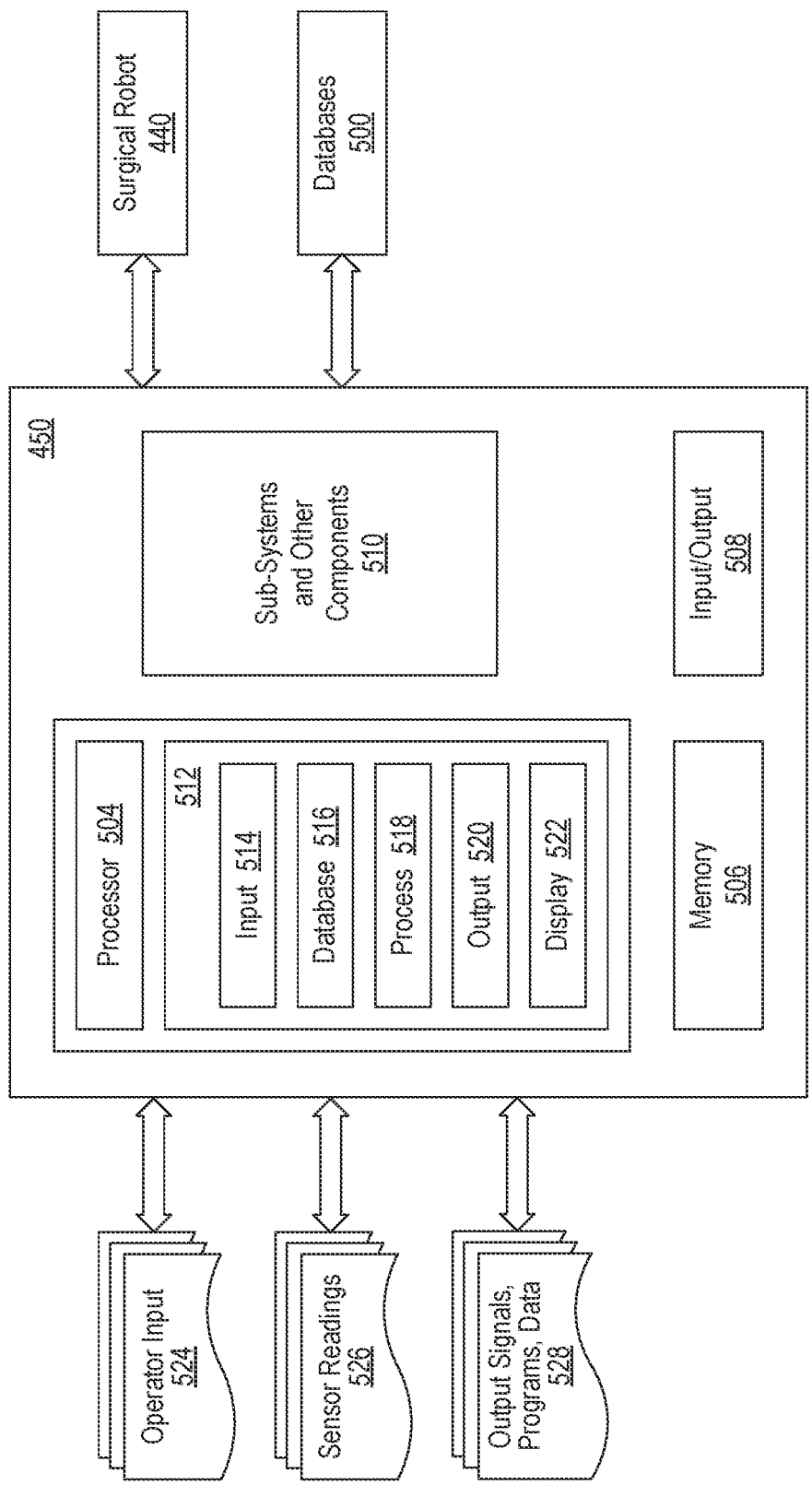
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices, and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein. In some embodiments, the memory 506 can store operational parameters and associated thresholds for surgical tools. The data can be retrieved from databases, such as third-party surgical equipment databases. In some embodiments, the data system 450 can determine whether the memory 506 includes operational parameters (e.g., speed, temperature, etc.) and associated data for a tool. In response to determining that operational parameters are not present, the database 550 can identify third party databases for retrieving such information. The data system 450 can retrieve, for example, protocols, updates, surgical tool information (e.g., recommended operational parameters and values, manufacturing information, etc.), or other information. The data system 450 can analyze sensor readings 526 to determine whether tool operation is within an acceptable range. In response to determining an operational parameter the tool meets a trigger threshold, the data system 450 can determine an action for the surgical tool. The data system 450 can send one or more output signals 528 to the tool to perform one or more actions. The actions can include, without limitation, adjusting operational speeds of the tool, stopping operation of the tool, a specific surgical step or action, combinations thereof, or the like.

The data system 450 can store machine learning engines disclosed herein. In some embodiments, the machine learning engines can be trained using training data sets for each tool. This allows the machine-learning engine to be configured to monitor data associated with each respective tool and to use the monitoring to determine additional actions. For example, a tool-specific machine learning engine can monitor data from a respective tool to determine whether a trigger event has occurred. The trigger event can be identified based on, for example, inputted trigger values, calculated trigger values, or the like. In some embodiments, training sets can include threshold values, trigger event threshold values, and other values associated with the tool, patient, surgical procedure, or the like. Surgical plans can include identified training sets for machine learning engines. This allows the robotic system to train machine learning engines as needed to enhance outcomes.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 2600. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room. The communication channel can be via a wireless network, wired connection, or the like.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

The systems and apparatuses discussed in connection with FIGS. 1-5 can use or incorporate the features, components, systems, or methods discussed in connection with FIGS. 6-13. For example, the system 100 discussed in connection with FIG. 1 can be configured to perform tool edge computing. For example, components of the operating room 102 (FIG. 1) can perform one or more edge computing processes to locally process data. In some embodiments, components of the operating room 402 of FIG. 4A can perform edge computing. For example, the end effector 452 of FIG. 4B can perform edge computing processes. This allows the user 421 to use locally provided sensor output of the end effector 452. In some embodiments, the data system 450 of FIG. 5 can be incorporated into surgical equipment to provide for localized edge computing. Systems, methods, and tools are discussed in connection with FIGS. 6-13.

Figure 6:
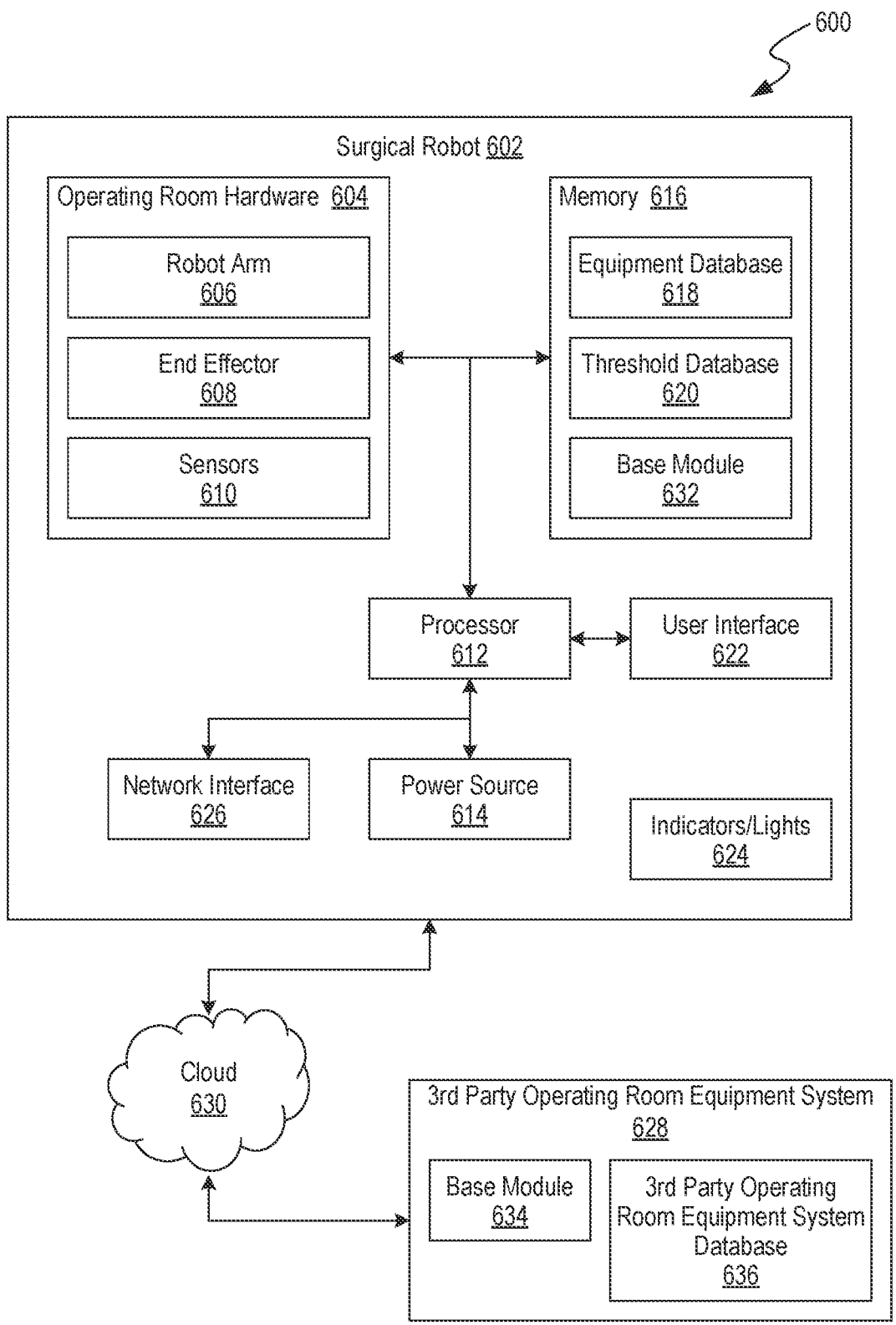
FIG. 6 illustrates a block diagram of a system for a computer modulated surgical tool edge sensor, according to an embodiment.

FIG. 6 illustrates a block diagram of a system 600 for a computer modulated surgical tool edge sensor, according to an embodiment. The system 600 may comprise a surgical robot 602 at a location where a surgery or an operation may be performed. The surgical robot 602 may comprise an operating room hardware 604 having a robot arm 606, and an end effector 608. In one embodiment, the operating room hardware 604 may be used for carrying out desired effects or performing the surgery or operation. Further, the robot arm 606 may be coupled with the end effector 608 to perform the surgery or the operation. It can be noted that the robot arm 606 is a type of mechanical arm, usually programmable, to perform a surgical procedure with more precision, flexibility, and control than is possible with conventional techniques. The robot arm 606 may be a Cartesian robot, a collaborative robot, an anthropomorphic robot, a SCARA robot, a spherical/polar robot, an articulated robot, or a parallel robot, without departing from the scope of the disclosure.

Further, the end effector 608 may include a sensor 610 to perform desired actions, such as analyzing real-time images at the tool edge and sending the analyzed images to the system 600. The robot arm 606 may be used to guide the sensor 610 to facilitate desired actions such as guiding a tool to perform a surgical. It can be noted that a various computational steps may be performed prior to the desired action, the computational steps including, but not limited to, edge computing, image processing, analyzing real-time images at the sensor, etc. It can also be noted that the end effector 608 may be, but not limited to, a surgical drill for boring through primarily hard structures such as bone, a surgical endoscope for probing internal structures, forceps for performing actions requiring gripping tissue or perform biopsies, a stapler for securing tissues from one another, an insufflator for injecting carbon dioxide into the abdominal cavity to create working space. In one embodiment, the sensor 610 may comprise a processing means for performing a computational analysis of data collected from the sensor 610 on the tool or the robot arm 606 to which the tool is affixed.

In one embodiment, the robot arm 606 may be a serial robot arm having a chain of links moved by joints that are actuated by motors. Further, robot arms may be typically classified in terms of the number of degrees of freedom. In one embodiment, the number of degrees of freedom may be equal to the number of joints that move the links of the robot arm. At least six degrees of freedom are required to enable the robotic hand to reach an arbitrary pose (position and orientation) in three-dimensional space. Additional degrees of freedom can allow changing the configuration of the link of the robot arm 606. The configuration of the robot arm 606 may be calculated by a mathematical process called Inverse kinematics, typically in terms of joint angles, given the desired pose of the robot hand in three-dimensional space.

Further, the surgical robot 602 may comprise a plurality of sensors, for sensing information related to the operating room hardware 604 being used in the robotic surgery procedure in an operating room (OR). It can be noted that each operating room hardware 604 may be coupled with at least one sensor of the plurality of sensors. In one embodiment, the plurality of sensors may be used to measure a plurality of parameters related to the operating room hardware 604, including, but not limited to, an orientation of the robot arm 606, a torque of the robot arm 606, a temperature of the surgical drill and tissues around the surgical drill, a power status of the robot arm 606, amount of force applied to the surgical drill. It can be noted that the plurality of sensors can include, for example, infrared cameras, lasers, force transducers, and other sensing components. Further, the plurality of sensors may comprise thermal and infrared sensors to detect continuously temperature and intensity of laser beams used to ablate tissues. In one embodiment, the plurality of sensors may correspond to patient monitoring sensors such as for monitoring heart rate, blood pressure, and blood oxygen concentration of the patient. In some embodiments, the plurality of sensors include components discussed in connection with operating room 102 of FIG. 1. The number, configuration, and operation (e.g., intercommunication, programming, sensing capabilities, etc.) can be selected based on the procedure to be performed.

In one embodiment, the operating room hardware 604 may be configured to perform surgery or operation using a surgical drill with at least one temperature sensor to detect the temperature of the surgical drill and the bone around the surgical drill. Further, the surgical drill may be provided with a plurality of sensors to detect different parameters related to the operation of the surgical drill. In one embodiment, the plurality of sensors may comprise, but not limited to, an accelerometer, a force transducer, a temperature or infrared sensor. The accelerometer may be configured to measure the orientation of the surgical drill. The force transducer may be provided to measure the amount of force applied to the surgical drill. It can be noted that the force may be axial force or lateral force. The temperature sensor or the infrared sensor may be configured to monitor the temperature of the surgical drill and/or the tissue or bone surrounding the surgical drill.

In another embodiment, the operating room hardware 604 may comprise an endoscope which may be used for probing internal structures. In one embodiment, the endoscope may comprise, but not limited to, an imaging device, and a channel for deploying additional tools such as forceps to perform biopsies. In one embodiment, the imaging device may be configured to monitor tissue structures when the endoscope is inserted inside the operation area. It can be noted that the imaging device and the channel may be used for navigation and diagnostic analysis. Further, the endoscope may be provided with the force transducer to detect forces applied to a leading edge of the endoscope and therefore, to prevent tearing a tissue. It can be noted that the force transducer coupled to the surgical endoscope may also help in identifying the location of the endoscope relative to the surrounding tissue.

In another embodiment, the operating room hardware 604 may comprise surgical forceps to perform actions related to gripping tissue and to perform biopsies. Further, the surgical forceps may be used to clamp bleeding blood vessels or hold tissues. The surgical forceps may also include a force transducer or accelerometer. In another embodiment, the operating room hardware 604 may comprise the surgical stapler to secure tissues to one another. It can be noted that other means of securing tissues may be employed. In one embodiment, the surgical stapler may be mounted with a plurality of sensors to detect and measure parameters such as, but not limited to, staple insertion force which is the force applied on the surgical staple while inserting staples and therefore, prevent excessive tearing of the tissue. In another embodiment, the surgical stapler may be mounted with a staple deformation device or the imaging device to measure the amount of deformation. It can be noted that the deformation device may be used to help in adjusting insertion force.

In another embodiment, the operating room hardware may be provided with the surgical insufflator for injecting carbon dioxide into the abdominal cavity to create working space. Further, the surgical insufflator may be mounted with the plurality of sensors, such as, a pressure monitoring sensor, which monitors the pressure of the carbon dioxide injected within the abdominal cavity. Further, the surgical insufflator may be provided with a gas composition sensor for monitoring changes in the composition of the gas inside the abdominal cavity. It can be noted that the gas composition sensor may sample or remove gasses within the abdominal cavity and prevent the use of incorrect gases. In one embodiment, the surgical insufflator may be provided with a flow rate monitor to detect and measure the rate at which the gas such as carbon dioxide is being injected into the abdominal cavity to identify unexpected leaks or excessive use of gas, etc.

Further, the system 600 may comprise a processor 612 for controlling functions of the operating room hardware 604. Further, the processor 612 may be configured to facilitate the operation of the operating room hardware 604. In one embodiment, the surgical robot 602 may comprise a power supply 614. It can be noted that the power supply 614 may be used to drive various hardware units of the operating room hardware 604. In one embodiment, the power supply 614 may be an internal power source to the operating room hardware 604. In another embodiment, the power supply 614 may be an external power source to the operating room hardware 604. It can be noted that the power supply 614 may be a battery. Further, the battery may be a Lithium polymer battery (Li—Po), due to its lightweight, high discharge rate, and good capacity. The power supply 614 may additionally comprise the components necessary to accept electricity from a source, such as a wall outlet operating at 120V or 240V alternating current, and to convert the source electricity into an output matching the requirements of the surgical robot 604, such as 12V direct current for driving motors, or 3- or 5-volt direct current for powering logic devices.

Further, the system 600 may comprise a memory 616. The memory 616 may comprise an equipment database 618 and a threshold database 620. The equipment database 618 may be configured to store data related to the plurality of sensors, and the operating room hardware data such as, but not limited to, the orientation of the robot arm 606, force applied on each of the sensor 610, the temperature of each sensor 610 and the tissue surrounding the tool, deformation occurred during stapling, the pressure of the gas injected into the abdominal cavity, gas flow rate, etc. In one embodiment, the equipment database 618 may be configured to store raw sensor data or an algorithm related to the orientation of the surgical drill measured by the accelerometer in X, Y, Z coordinates. In another embodiment, the equipment database 618 may be configured to store the angle of the surgical drill measured by the plurality of sensors. The threshold database 620 may be configured to store information related to a plurality of data ranges and threshold values of different parameters related to one or more surgical tools. In one embodiment, the threshold database 620 may be configured to the parameters related to rules and actions required during surgery. The threshold database 620 may be configured to store instructions related to each surgical component of the operating room hardware 604. It can be noted that the instructions may be related to metadata ranges and thresholds of each component of the operating room hardware 604 while performing a particular surgery.

Further, the memory 616 may comprise short-term volatile memory and/or long-term persistent memory. Further, the equipment database 618 may be configured to store parameters related to the robot arm 606. It can be noted that the parameters related to the robot arm 606 may be, but not limited to, the orientation of the robot arm 606, input power supplied to the robot arm 606, duty cycle, etc. Further, the equipment database 618 may be configured to store a plurality of types of sensors 610 employed during a surgical procedure. It can be noted that there may be a library of workflow, operations, and disease states to treat in the equipment database 618. In one embodiment, the library workflows may include different surgical procedures needed to be performed to treat a specific disease, such as but not limited to, ablation of scar tissue, removal of cancerous cells, etc. Further, the equipment database 618 and the threshold database 620 may receive sensed data from the plurality of sensors, for performing calculations and providing recommendations based on the sensed data.

In one embodiment, the equipment database 618 may be configured to store parameters related to the robot arm 606. For example, different types of parameters of the surgical robot 602 suited for different types of surgical procedures are also stored in the equipment database 618. Further, the equipment database 618 may be useful to set up the robot arm 606 according to the surgery being conducted. Further, equipment database 618 is shown in FIG. 7. For example, the equipment database 618 stores information related to patient 1 at time 2 pm, the orientation of the robot arm 606 at 2 degrees from vertical axis and 5 degrees from horizontal axis for bone replacement, and a force of 10N applied axially with the temperature of the surgical drill to be 25 degrees Celsius and the temperature of the bone surrounding the surgical drill to be 36.5 degrees Celsius; at 4 pm, the orientation of the robot arm 606 at 2 degrees from vertical axis and 5 degrees from horizontal axis for bone graft, and a force of 15N applied laterally with the temperature of the surgical drill to be 27 degrees Celsius and the temperature of the bone surrounding the surgical drill to be 37.5 degrees Celsius.

The threshold database 620 may store parameters related to thresholds of each operating room hardware 604 while performing the surgical procedure. Further, the threshold database 620 may be configured to receive information from the plurality of sensors mounted over each operating room hardware 604 and create metadata ranges for each parameter received. Further, the threshold database 620 may be configured to create new rules and actions for each operating room hardware 604 based on the received parameters from the plurality of sensors. In one example, the threshold database 620 creates metadata ranges and thresholds for the surgical drill that a threshold limit of force to be applied during a bone graft procedure ranges between 10N to 20N, and when the surgical drill implies more force than 20N, the threshold database 620 signals the robot arm 606 to stop the operation. In another example, the threshold database 620 sets rules and actions for the surgical drill while performing an operation such that, if the temperature of the surgical drill detected by the temperature sensor is more than the threshold temperature limit of 29 degrees Celsius or the temperature of the surrounding tissue/bone is more than 38 degrees Celsius, the threshold database 620 transmits a signal to the robot arm 606 to immediately stop the operation and alert the doctor. In some embodiments, the threshold database 620 can include thresholds, threshold ranges, or other values determined using, for example, one or more machine learning engines. This allows thresholds to be generated based on training sets from similar procedures. If a threshold is not known for a procedure or patient, the system can generate thresholds for the database 620 prior to the surgical procedure. A surgical team can review the threshold values to approve, modify, or re-train the machine learning engine. This allows the surgical team to define criteria for monitoring patients and surgical steps. In some embodiments, the threshold database 620 can store parameters related to surgical steps, types of procedures, patient-specific thresholds, surgical plan thresholds, or combinations thereof.

The surgical robot 602 may comprise a user interface 622 for displaying controls related to the surgical procedure. Further, the user interface 622 may comprise, but not limited to, a display device such as a touch screen to display controls related to surgery, and analysis of data, an audio device such as speakers and a microphone to send and receive instructions related to operating room hardware 604 and a surgical procedure, and a haptic device to provide control feedback. In one embodiment, the user interface 622 may be configured to display images of the area captured by the plurality of sensors of the operating room hardware 604. In one embodiment, the audio devices may include speakers and microphones for interacting with the operating room hardware 604. In one embodiment, the user interface 622 may include imaging device outputs. In some embodiments, the user interface 622 can be in the form of a video display (e.g., video display 318 of FIG. 3), a display (e.g., display 422 of FIG. 4A), a viewer (e.g., viewer 430 of FIG. 4B), or another suitable viewing device.

Further, the surgical robot 602 may comprise a plurality of indicators 624 coupled to the user interface 622 to alert the doctor when a dangerous situation has occurred during surgery. In one embodiment, the plurality of indicators 624 may include different color lights which may indicate the situation of the surgery being performed. For example, a green light indicates that the operation/surgery is proceeding according to the desired parameters and within the threshold limit of each parameter of each operating room hardware 604, a red light indicates that a dangerous situation has occurred and the doctor has been alerted, and a yellow light indicates that the operation is nearing a dangerous situation.

The surgical robot 602 may further comprise a network interface 626. In one embodiment, the network interface 626 may be configured to facilitate communication of the surgical robot 602 to a third party ($3^{rd}$) operating room equipment system 628 via a cloud network 630. In one embodiment, the network interface 626 of the surgical robot 602 may be a radio communication or other wired or wireless communication. It can be noted that the network interface 626 may communicate with the cloud network 630 to be implemented using a collection of server devices to provide one or more services to coupled devices and data sources. Further, the network interface 626 may be a wired and/or a wireless network. The network interface 626, if wireless, may be implemented using communication techniques such as Visible Light Communication (VLC), Worldwide Interoperability for Microwave Access (WiMAX), Long Term Evolution (LTE), Wireless Local Area Network (WLAN), infrared (IR) communication, radio waves, and other communication techniques, known in the art.

The network interface 626 may be communicatively coupled to the robot arm 606, the end effector 608, the sensor 610, the processor 612, the memory 616, the plurality of sensors, the power supply 614, and the user interface 622 for real-time assistance in the operating room (OR). The network interface 626 may also be synchronized with the equipment database 618, and the threshold database 620, to store information associated with the operating room hardware 604. It can be noted that the network interface 626 may be in communication with a base module 632 of the surgical robot 602.

Further, the $3^{rd}$ party operating room equipment system 628 may also comprise a base module 634 and a $3^{rd}$ party operating room equipment system database 636. In one embodiment, the $3^{rd}$ party operating room equipment system 628 may be remotely located from the surgical robot 602. The $3^{rd}$ party operating room equipment system 628 may be communicatively coupled with the surgical robot 602 over the cloud network 630. Further, the base module 634 of the $3^{rd}$ party operating room equipment system 628 may comprise an initiation module configured to provide an initial connection of the $3^{rd}$ party operating room equipment system 628 with the surgical robot 602 to retrieve information from the equipment database 618 such as, but not limited to, operating parameters, acceptable ranges (e.g., operational speeds, temperatures, forces, etc.) of the tool, such as a surgical drill. In one embodiment, the base module 634 may retrieve information from the equipment database 618 related to the doctor and the patient. Further, the $3^{rd}$ party operating room equipment system database 636 of the $3^{rd}$ party operating room equipment system 628 may be configured to store the retrieved information from the equipment database 618 and the threshold database 620.

Further, the base module 634 of the $3^{rd}$ party operating room equipment system 628 may comprise a handshake with the surgical robot 602 to enable sending and receiving information related to the operating room hardware 604, such as surgical drill, endoscope, etc. In one embodiment, the $3^{rd}$ party operating room equipment system database 636 of the $3^{rd}$ party operating room equipment system 628 may be constantly updated in real-time according to the information received from the equipment database 618 and the threshold database 620, such as updated analysis of data, thresholds, rules, and actions. Further, the base module 634 of the $3^{rd}$ party operating room equipment system 628 may be configured to provide alerts to the doctor when an emergency has occurred.

FIG. 7 illustrates an equipment database for a system in accordance with embodiments of the technology. The equipment database 618 can include target values for surgical equipment, surgery requirements, operating values (e.g., temperature of equipment, applied forces, deformation, pressure, etc.), orientations, and other information. The drill is surgical equipment with an acceptable range of operating temperatures of, for example, 25-35° C. The surgical equipment can include one or more temperature sensors for monitoring the temperature of the drill, tissue, etc. A threshold acceptable temperature of tissue can be, for example, 36.5° C. Other threshold acceptable temperatures of tissue can be inputted by a user.

The equipment database 618 can include an acceptable range of applied forces of, for example, 10-20 newtons, or other suitable ranges of force. The acceptable range of orientations can be within, for example, 2 degrees of vertical, 2 degrees of horizontal, 5 degrees of horizontal, or other suitable orientations based on the position of patient, surgical technique, etc. The equipment database 618 can include surgical procedures for surgical equipment. For example, an abdomen surgery can be associated with forceps. The acceptable ranges associated for forceps can be retrieved as needed. In some procedures, the acceptable ranges for the forceps can include, without limitation, an acceptable temperature range of forceps of 25-30° C., tissue temperatures of 30-40° C. (e.g., a threshold tissue temperature can be 36.5. ° C.), maximum acceptable force can be 10 newtons, or combinations thereof. The acceptable ranges can be modified by a system or user based on real-time data.

FIG. 8 illustrates a threshold database for a system in accordance with embodiments of the technology. The threshold database 620 can include one or more actions associated with detected events. The actions can include adjusting operation of surgical equipment. For example, a drill can be slowed down when a trigger temperature is reached. The trigger temperature can be, for example, a temperature of 37° C. In some embodiments, the threshold database 620 can include minimum threshold temperatures, maximum threshold temperatures, or other temperatures. The trigger temperature can be selected based on the procedure to be performed. For example, the trigger temperature for bone replacement can be 37° C. The trigger temperature for a drill used for providing insertion paths can be 32° C. to limit or prevent excessive heating around the access site. FIG. 8 shows actions (e.g., slowing drills) when surgical equipment (e.g., endoscopes, forceps, staplers, insufflator, etc.) detect trigger temperatures. Each component in the surgical procedure can detect temperatures associated with a trigger temperature. Additionally, or tentatively, the surgical equipment shown in FIG. 8 can detect and monitor other parameters, such as tissue temperatures, applied forces, or the like.

Figure 9A:
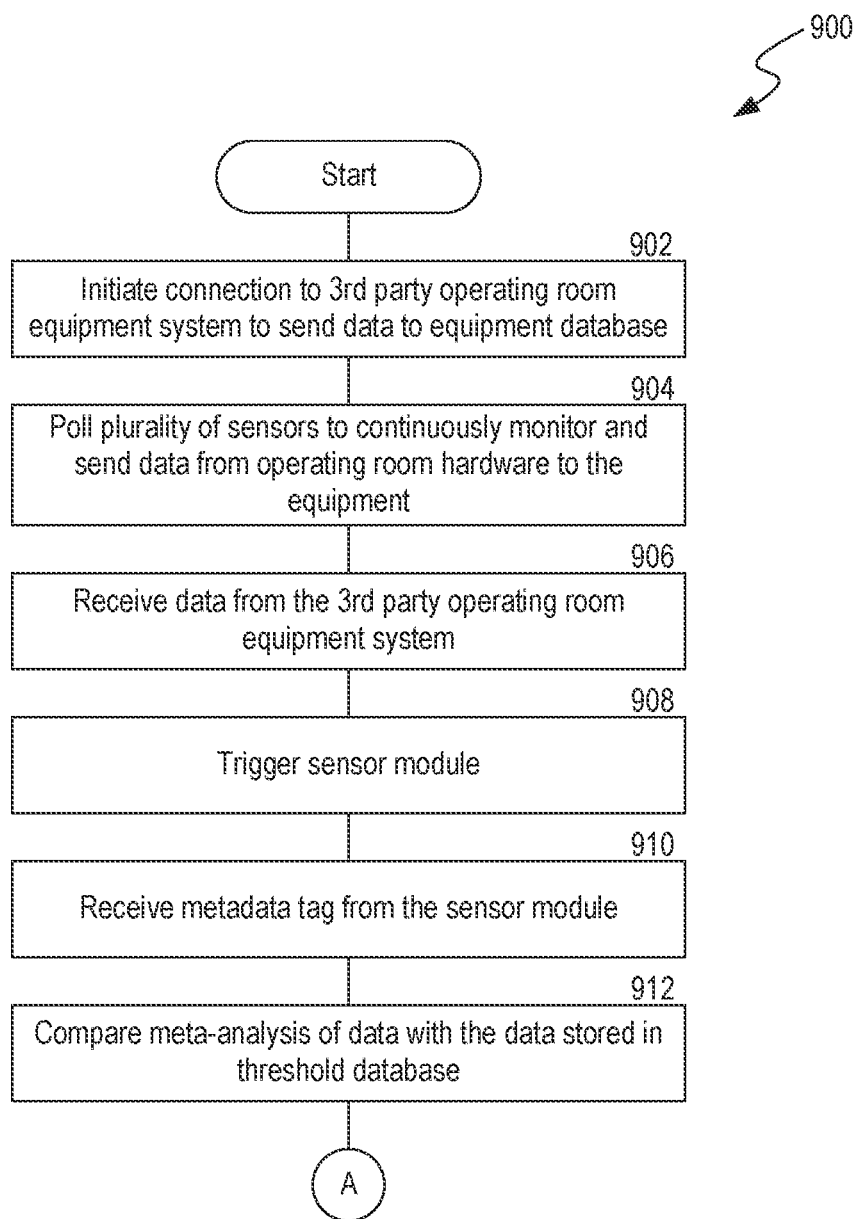
FIGS. 9A and 9B illustrate flow charts showing a method of operation of a base module of surgical robot, according to an embodiment.
Figure 9B:
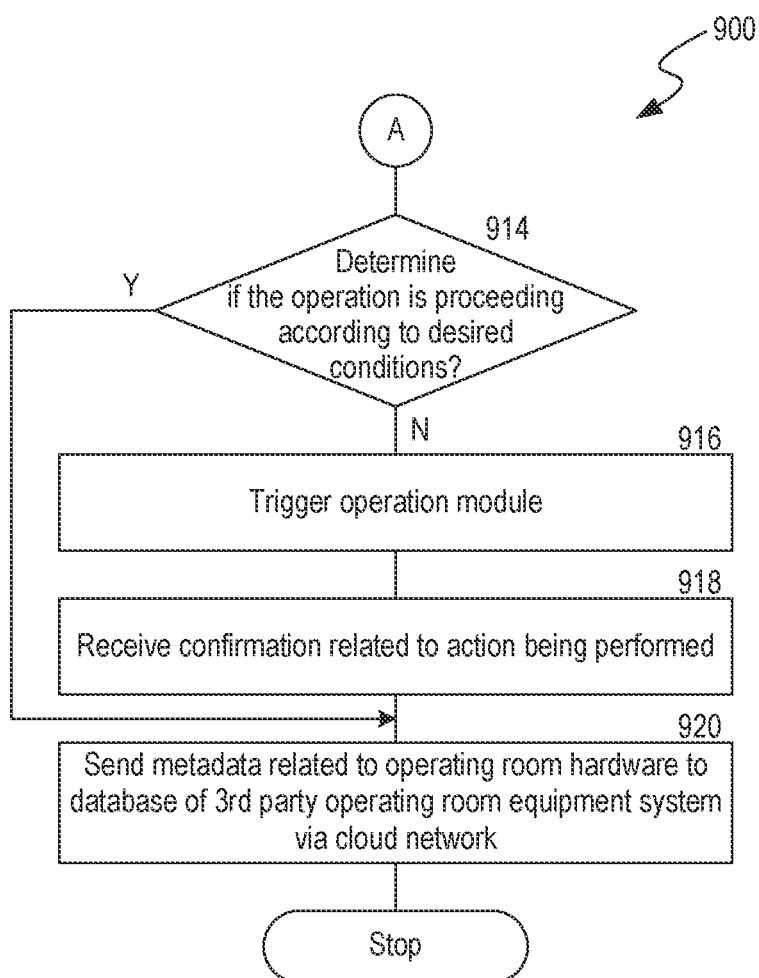

The base module 632 of the surgical robot 602 may be configured to retrieve information related to the surgical tools, from the $3^{rd}$ party operating room equipment system database 636. Further, the base module 632 may be configured to perform an operation of the surgical robot 602 in real-time. Further, the base module 632 of the surgical robot 602 may be described as shown in FIG. 9A and FIG. 9B, which illustrate steps during a surgical procedure. FIG. 9A and FIG. 9B are explained in conjunction with FIG. 6, FIG. 7, FIG. 8, FIG. 10, FIG. 11, FIG. 12, and FIG. 13. It should also be noted that in some alternative implementations, the functions noted in the blocks may occur out of the order noted in the drawings. For example, two blocks shown in succession in FIG. 9A and FIG. 9B may be executed substantially concurrently or the blocks may sometimes be executed in the reverse order, depending upon the functionality involved. In addition, the process descriptions or blocks in flow charts should be understood as representing decisions made by a hardware structure such as a state machine.

Firstly, the base module 632 may initiate a connection to the $3^{rd}$ party operating room equipment system 628 to send data to the equipment database 618, at step 902. In one embodiment, the base module 632 may facilitate communication between the surgical robot 602 and the $3^{rd}$ party operating room equipment system 628 prior to the procedure of the surgery so that the $3^{rd}$ party operating room equipment system 628 may send data related to the equipment database 618. In one embodiment, the base module 632 may retrieve data from the $3^{rd}$ party operating room equipment system database and send the retrieved data to the equipment database 618 prior to the start of the operation. It can be noted that the retrieved data may be operational parameters and firmware or software updates for the tool. Further, the $3^{rd}$ party operating room equipment system may be an external system, which may be created and maintained by the manufacturer of a surgical tool.

Further, the base module 632 may poll the plurality of sensors to continuously monitor and send data, from the operating room hardware, to the equipment database, at step 904. In one embodiment, the base module 632 may continuously poll the plurality of sensors of each operating room hardware 604 to detect and monitor raw sensor data and then send to the equipment database 634 in real-time. For example, the temperature sensor of the surgical drill continuously monitors the temperature of the surgical drill as 27 degrees Celsius and the temperature of the bone/tissue surrounding the surgical drill as 36.5 degrees Celsius. In another example embodiment, the base module 632 sends that the temperature of the surgical drill while boring into the bone of Alex is 27 degrees Celsius and the temperature of the surrounding tissue/bone of Alex is 36.5 degrees Celsius. Further, the base module 632, at step 906, may receive data from the $3^{rd}$ party operating room equipment system. In one embodiment, the base module 632 may use the received data to assist the surgeon during the surgical procedure. Successively, the base module 632 may trigger the sensor module at step 908. It can be noted that the operation of sensor module is described in FIG. 10.

Figure 10:
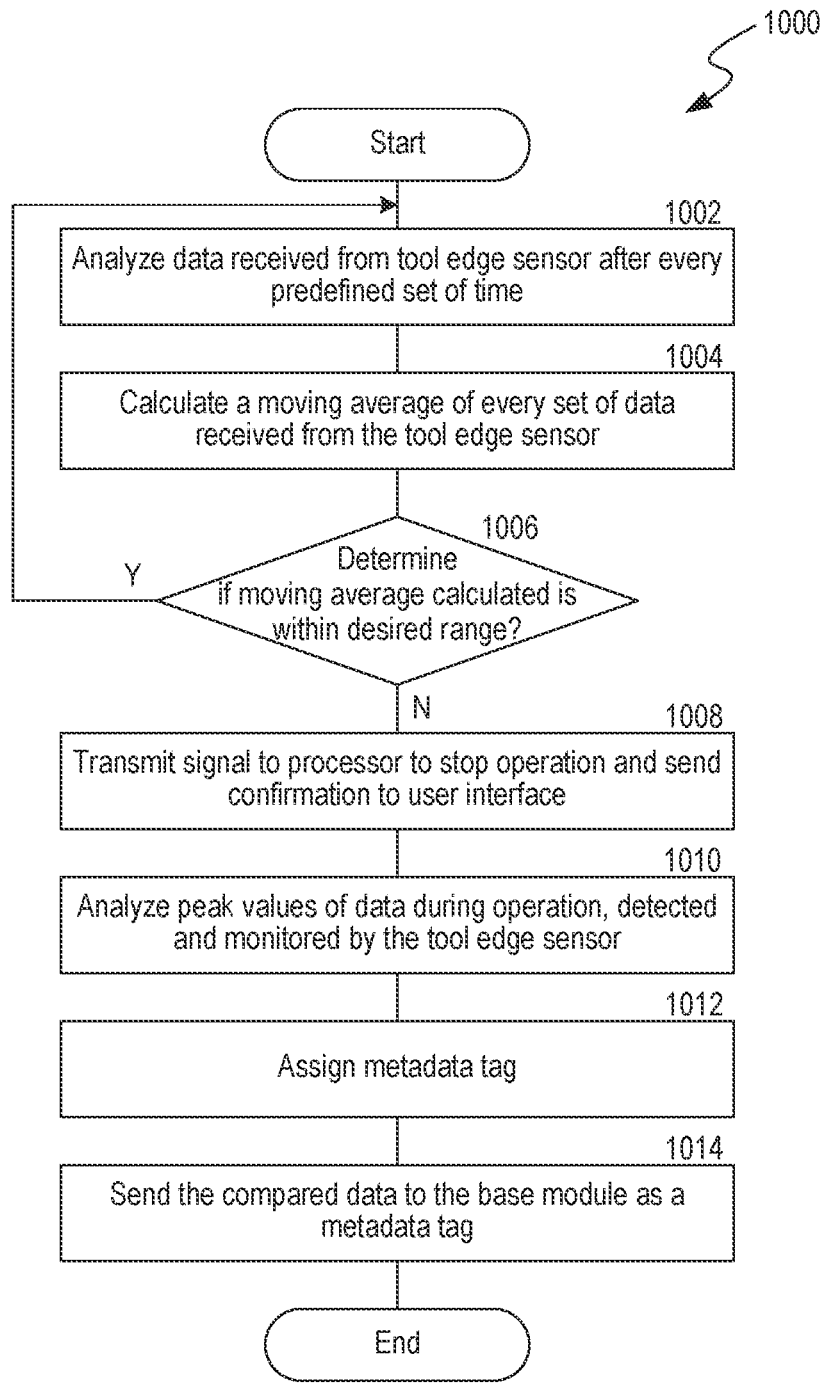
FIG. 10 illustrates a flow chart showing a method of operation of a sensor module, according to an embodiment.

FIG. 10 illustrates a flow chart showing a method 1000 of operation of the sensor module, according to an embodiment. FIG. 5 is described in conjunction with FIG. 6, FIG. 7, FIGS. 8, FIGS. 9A-9B, FIG. 11, FIG. 12, and FIG. 13. In one embodiment, the sensor module may be configured to create metadata from the data received from the sensor 610 and then compare the metadata with threshold data from the threshold database 620. It should also be noted that in some alternative implementations, the functions noted in the blocks may occur out of the order noted in the drawings. For example, two blocks shown in succession in FIG. 10 may in fact be executed substantially concurrently or the blocks may sometimes be executed in the reverse order, depending upon the functionality involved. In addition, the process descriptions or blocks in flow charts should be understood as representing decisions made by a hardware structure such as a state machine.

At first, the sensor module may collect and analyze data received from the sensor 610 after every predefined set of time, at step 1002. In one embodiment, the sensor module may receive data from the sensor 610 such as temperature sensor, imaging device, force transducer, accelerometer, etc., mounted on the end effector 608 of the robot arm 606. In one embodiment, the predefined set of time may be programmed into each sensor 610 to monitor and/or detect changes during surgery performed by the operating room hardware 604. For example, the sensor module analyzes data received from the sensor 610 after every 5 milliseconds (ms). Further, the sensor module may calculate a value (e.g., moving average) of every set of data received from the sensor 610, at step 1004. In one embodiment, the sensor module may create metadata by calculating the value (e.g., moving average) of the data detected and monitored by the sensor 610. In one embodiment, the set of data received from the sensor 610 may include, a plurality of frames detected by the imaging device when the surgical endoscope is inserted into the body of a patient or the force of surgical endoscope. In another embodiment, the sensor module calculates average of force of surgical endoscope, every 10 seconds, such as 10N for first five seconds and 12 N for the consecutive 5 seconds.

Further, the sensor module may determine if the value (e.g., moving average) calculated is within the desired range, at step 1006. In one embodiment, the sensor module may determine whether the operating room hardware 604 is operating the end effector 608 within the desired range of parameters detected by the sensor 610. It can be noted that the desired range for each operating room hardware 604 may vary according to each surgery/operation. In one case, the sensor module may determine that the value (e.g., moving average) of the data is not within the desired range. For example, the sensor module determines that the surgical endoscope is applying 12N of force which is 2N more than the threshold limit of force 10N, so that the imaging device captures 5 frames in 5 ms. In this case, the sensor module may proceed to step 1008 to transmit a signal to the processor 612 to stop the operation and send a notification to the user interface 622 with the plurality of indicators 624 displaying yellow light for stop and then red light that the emergency has occurred and the doctor at the user interface 622 may intervene to change controls of the robot arm 606.

In another case, the sensor module may determine that the value (e.g., moving average) of the data is within the desired range. For example, the sensor module determines that the surgical endoscope is applying 10N of force with the orientation of the robot arm at 2 degrees from vertical axis and 5 degrees from horizontal axis, which is within the threshold limit of 10N and threshold orientation of 2 degrees from vertical axis and 5 degrees from horizontal axis. In this case, the sensor module may proceed to step 1010 to analyze peak values of the data during the operation, detected and monitored by the sensor 610. In one embodiment, the sensor module may analyze peak values of the data during the operation such as the threshold value of force or temperature or orientation, exceeded by the operating room hardware 604 during the operation/surgery. In another embodiment, the sensor module may analyze peak values when the operating room hardware 604 may exceed the desired range for the operation/surgery. For example, the sensor module analyses that the force detected by the force transducer is more than 2N laterally than the threshold limit of force 10N, and the temperature of the endoscope is 33 degrees Celsius which is 1 degree Celsius more than the threshold temperature limit of 32 degrees Celsius.

Further, the sensor module may assign a metadata tag to calculated data, such as a moving average or peak value, at step 1012. In one embodiment, the sensor module categorizes each data with a metadata tag indicating whether the data indicates normal operation, a warning condition, an abnormal condition, etc. For example, the sensor module assigns a metadata tag for the orientation of the robot arm 606 indicates orientation of robotic arm 606 matches the threshold orientation. Further, the sensor module may send the data and metadata tag to the base module 632, at step 1014. For example, the sensor module sends the metadata tag for the orientation of the robot arm 606 that the orientation of robotic arm 606 matches the threshold orientation.

Further, the base module 632 may receive the metadata tag for the orientation of the robot arm 606, at step 910. For example, the base module 632 receives the metadata tag for orientation of the robot arm indicating that the orientation is in a warning state and nearing a danger threshold. Further, the base module 632 may compare the analysis of data with the data stored in the threshold database 620, at step 912. For example, the base module 632 compares that the temperature of the surgical drill is 27 degrees Celsius when the orientation of the robot arm 606 is 2 degrees from vertical axis and 5 degrees from horizontal axis, which is below the threshold temperature limit of 32 degrees Celsius.

Successively, the base module 632 may determine if the operation is proceeding according to desired conditions, at step 914. In an embodiment, the base module 632 may determine whether the operating room hardware 604 is performing functions within the threshold limits of the threshold database 620. In one case, the base module 632 may determine if the operation is not proceeding according to the desired conditions. For example, the base module 632 determines that the surgical drill is applying 16N force laterally over the bone which is 1N more than the threshold limit of force, with the orientation of the robot arm 606 as 2 degrees from vertical axis and 5 degrees from horizontal axis which raises the temperature of the surgical drill to 32 degrees Celsius equal to the threshold limit of temperature and the temperature of the bone surrounding the surgical drill rises to 38.5 degrees Celsius. In this case, the base module 632 proceeds to step 916, to trigger the operation module.

Figure 11:
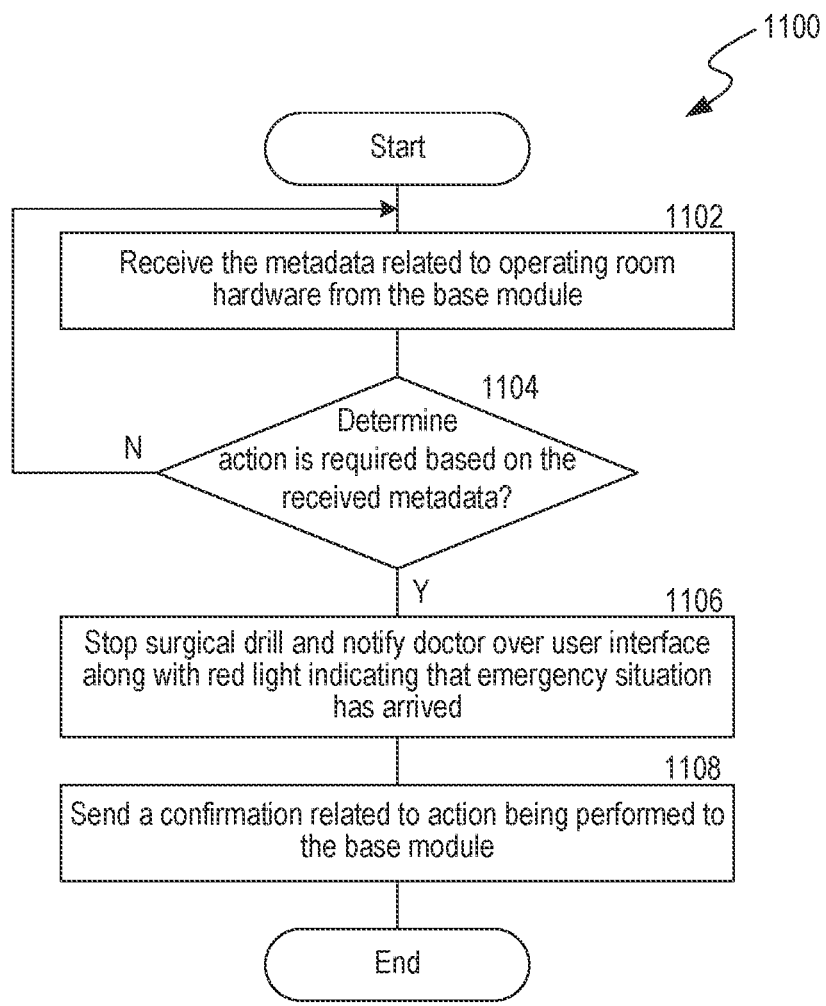
FIG. 11 illustrates a flow chart showing the method of operation of an operation module, according to an embodiment.

It can be noted that the operation module may be described in conjunction with FIG. 11. FIG. 11 illustrates a flow chart of a method 1100 performed by an operation module. It should also be noted that in some alternative implementations, the functions noted in the blocks may occur out of the order noted in the drawings. For example, two blocks shown in succession in FIG. 11 may in fact be executed substantially concurrently or the blocks may sometimes be executed in the reverse order, depending upon the functionality involved. In addition, the process descriptions or blocks in flow charts should be understood as representing decisions made by a hardware structure such as a state machine.

At first, the operation module may receive the metadata related to the operating room hardware 604 from the base module 632, at step 1102. In one embodiment, the operation module may receive the metadata received from the base module 632 for each operation to be performed. For example, the operation module receives that the orientation of the robot arm 606 to which the surgical drill is mounted is 2 degrees from vertical axis and 5 degrees from horizontal axis, and the temperature of the surgical drill is 25 degrees Celsius corresponding to the temperature of the bone surrounding the surgical drill is 35.5 degrees Celsius. Further, the operation module may determine if action is required based on the received metadata, at step 1104. In one embodiment, the operation module may perform actions according to the metadata received from the base module 632. In one case, the operation module may determine that no action is required because the metadata tags indicate that the drill is operating normally. For example, the operation module determines that the received metadata related to the orientation of the robot arm 606 is which is within the threshold orientation of the surgical drill, and the temperature of the surgical drill is 27 degrees Celsius which is also within the threshold limit of the temperature of the surgical drill, then no external action is required, as the operation is proceeding according to the desired conditions. In this case, the operation module may be redirected back to the step 1102 to again receive metadata from the base module 632.

In another case, the operation module may determine that action is required based on the metadata received from the base module 632. For example, the operation module determines that the received metadata related to force applied by the surgical drill on the bone is 12N which 2N more than the threshold limit of 10N force, and the temperature of the surgical drill 33 degrees Celsius which is also 1 degree Celsius more the threshold limit of temperature 32 degree Celsius of the surgical drill, then the operation module may proceed to step 1106 to stop the surgical drill and notify the doctor over the user interface 622 along with the red light indicating that the emergency has arrived. For example, the operation module stops the surgical to let the surgical drill cool down and change the controls of the robot arm 606 to apply the force of 10N which is within the threshold limit of force. Further, the operation module may send a notification related to the action being performed to the base module 632, at step 1108. In one embodiment, the operation module may send the notification of the actions such as changing controls of the operating room hardware 604 to be within the threshold limit. For example, the operation module sends the notification that surgical drill is stopped as soon as the force applied by the robot arm exceeds 10N and lets the surgical drill to cool down due to the rise in temperature to 33 degrees Celsius.

Further, the base module 632 may receive the notification related to action being performed, from the operation module, at step 918. For example, the base module 632 receives notification that surgical drill is stopped as soon as the force applied by the robot arm exceeds 10N and lets the surgical drill cool down.

In another embodiment, at step 914, the base module 632 may determine that the operation is proceeding to according to the desired conditions. For example, the base module 632 determines that the orientation of the robot arm 606 is 2 degrees from vertical axis and 5 degrees from horizontal axis, and the surgical drill is exerting 12N of force over the bone with the temperature of the surgical drill at 28 degrees Celsius and the temperature of the bone surrounding the surgical drill is 36.5 degrees Celsius. In this case, the base module 632 proceeds to step 920 to send the data related to the operating room hardware 604 to the 3$^{rd}$ party operating room equipment system database 636 via the cloud network 630.

Figure 12:
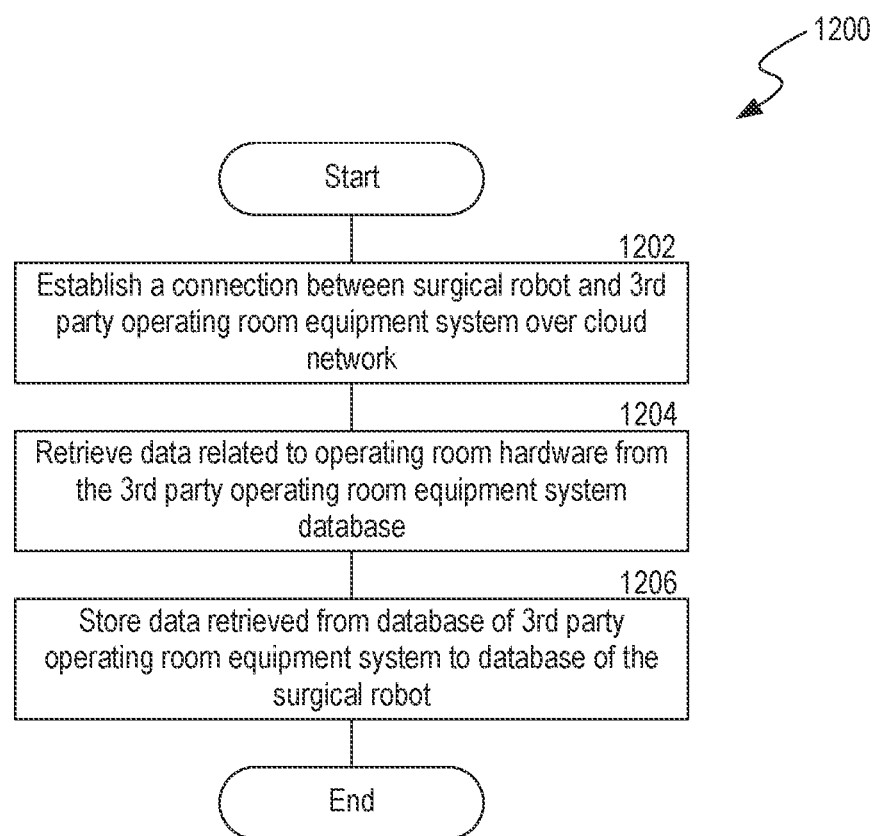
FIG. 12 illustrates a flow chart showing a method of operation of a communication module, according to an embodiment.

FIG. 12 illustrates a flow chart of a method 1200 performed by a communication module. It can be noted that the communication module is explained in conjunction with FIG. 10. It should also be noted that in some alternative implementations, the functions noted in the blocks may occur out of the order noted in the drawings. For example, two blocks shown in succession in FIG. 12 may in fact be executed substantially concurrently or the blocks may sometimes be executed in the reverse order, depending upon the functionality involved. In addition, the process descriptions or blocks in flow charts should be understood as representing decisions made by a hardware structure such as a state machine.

At first, the communication module may establish a connection between the surgical robot 602 and the 3$^{rd}$ party operating room equipment system 628 over the cloud network, at step 1202. In one embodiment, the communication module may facilitate connection to the 3$^{rd}$ party operating room equipment system 628 using the cloud network when an intervention over the surgical procedure is required. For example, the communication module facilitates connection to the 3$^{rd}$ party operating room equipment system while performing the bone replacement surgery of Alex, a complication is detected by the sensor 610, and therefore the 3$^{rd}$ party operating room equipment system intervention is required. Further, the communication module may retrieve data related to the operating room hardware 604 from the 3$^{rd}$ party operating room equipment system database 636, at step 1204. In one embodiment, the communication module may retrieve data related to surgery/operation being performed using the operating room hardware such as surgical drill mounted over the robot arm 606. For example, the communication module retrieves performing the bone replacement surgery of Alex, a complication is detected by the sensor 610, and therefore the 3$^{rd}$ party operating room equipment system intervention is required.

Further, the communication module may store the data retrieved from the 3$^{rd}$ party operating room equipment system database 636 of the 3$^{rd}$ party operating room equipment system 628 to the database 632 of the surgical robot 602, at step 1206. In one embodiment, the retrieved data may comprise of threshold values or other operating parameters for surgical equipment. For example, the communication module stores the threshold value of force of 12N of the robotic arm 606.

Figure 13:
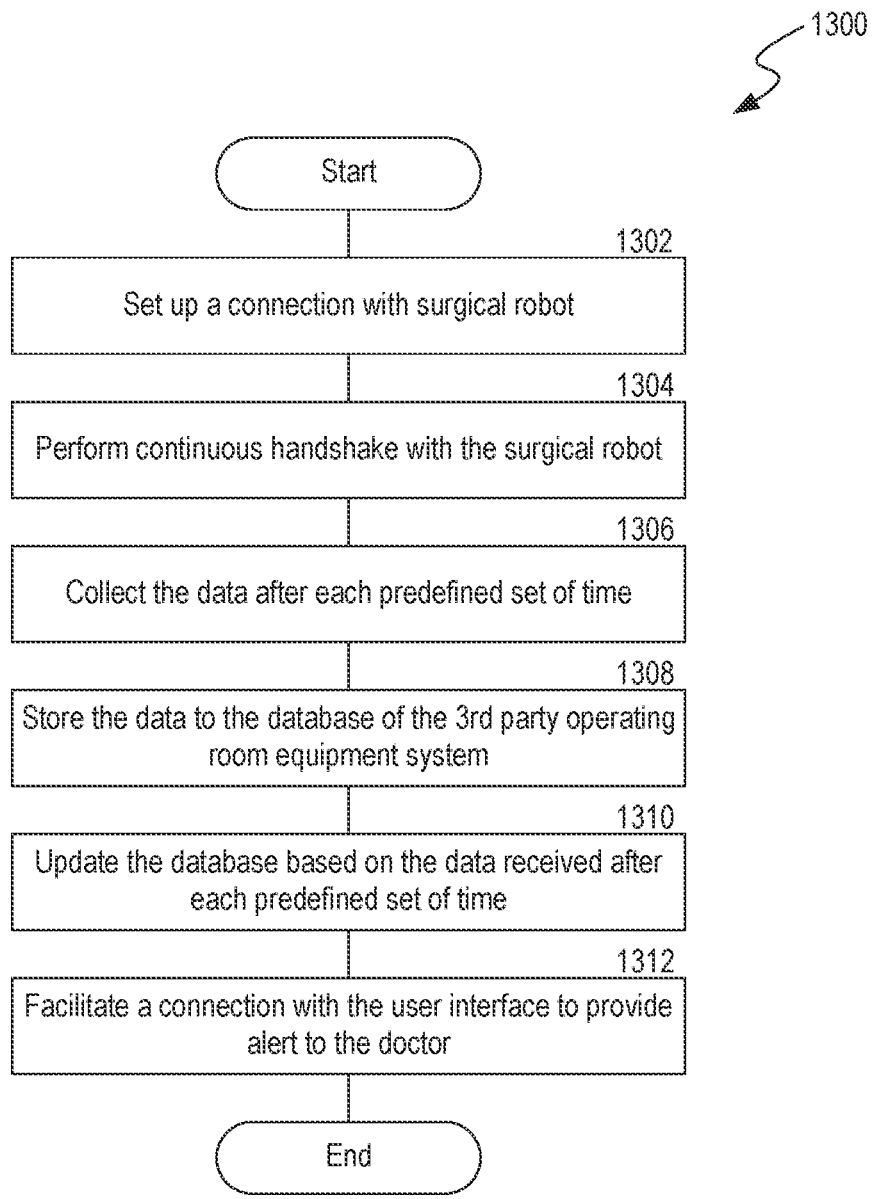
FIG. 13 illustrates a flow chart showing a method of operation of a base module of a $3^{rd}$ party operating room equipment system, according to an embodiment.

Further, the base module 632 of the surgical robot 602 may communicate with the base module 634 of the 3$^{rd}$ party operating room equipment system 628, after the connection may be established by the communication module, as described in FIG. 12. Further, the 3$^{rd}$ party operating room equipment system 628 may function in a similar manner as the base module 632 of the surgical robot 602. FIG. 13 illustrates a flow chart of a method 1300 performed by the base module 634 of the 3$^{rd}$ party operating room equipment system 628. It should also be noted that in some alternative implementations, the functions noted in the blocks may occur out of the order noted in the drawings. For example, two blocks shown in succession in FIG. 13 may in fact be executed substantially concurrently or the blocks may sometimes be executed in the reverse order, depending upon the functionality involved. In addition, the process descriptions or blocks in flow charts should be understood as representing decisions made by a hardware structure such as a state machine.

At first, the base module 634 may set up a connection with the surgical robot 602 to retrieve information related to operating room hardware 604, at step 1302. In one embodiment, the base module 634 may facilitate connection to the surgical robot 602 to retrieve data related to the operating room hardware 604 from the 3$^{rd}$ party operating room equipment system database 636. For example, the base module 634 retrieves data that Alex is being diagnosed with the bone disease and the bone replacement is the treatment performed using the surgical drill over the robot arm 606. Further, the base module 634 may perform continuous handshake with the surgical robot 602, at step 1304. In one embodiment, the handshake with the surgical robot 602 may refer to the constant transfer of data with the 3$^{rd}$ party operating room equipment system 628.

Further, the base module 634 may collect the data collected by the sensor 610 after each predefined set of time, at step 1306. In one embodiment, the base module 634 may collect the data detect by the sensor 610 such as temperature sensor, imaging device, accelerometer, and force transducer, mounted on the robot arm 606. In one embodiment, the predefined set of time may be preprogrammed within the sensor 610 to send data after monitoring for some time. For example, the base module 634 collects data related to the surgical drill detected by the sensor 610 after every 5 ms of time, that the temperature of the surgical drill is 29 degrees Celsius by applying the force of 10N laterally with the orientation of the robot arm 606 as 2 degrees from vertical axis and 5 degrees from horizontal axis. Further, the base module 634 may store continuously the data to the 3$^{rd}$ party operating room equipment system database 636, at step 1308. In one embodiment, base module 634 may store the data continuously after each predefined set of times in the 3$^{rd}$ party operating room equipment system database 636. For example, the base module 634 stores the data related to the surgical drill, after every 5 ms of time, that the temperature of the surgical drill is 29 degrees Celsius by applying the force of 10N laterally with the orientation of the robot arm 606 as 2 degrees from vertical axis and 5 degrees from horizontal axis. In one embodiment, the base module 634 may transfer data to the 3$^{rd}$ party operating room equipment system database 636 at a conclusion of the procedure or at a longer interval period, like an hour or a day.

Further, the base module 634 may update the 3$^{rd}$ party operating room equipment system database 636 based on the data received after each predefined set of time, at step 1310. In one embodiment, the base module 634 may update the 3$^{rd}$ party operating room equipment system database 636 that after each predefined set of time, the robot arm 606 may tilt causing a drift in orientation, and therefore, may set a new rule for orientation of the robot arm 606 to compensate for the drift. In another embodiment, the base module 634 may update the 3$^{rd}$ party operating room equipment system database 636 about the new rules to ensure safety during the operating procedure. For example, the base module 634 updates the 3$^{rd}$ party operating room equipment system database 636 that after every 5 ms of data received from the sensor 610, the orientation of the robot arm 606 is tilted to 2 degrees from vertical axis and 5 degrees from horizontal axis, and therefore, to ensure the safety of the bone (of Alex), the force applied by the surgical drill is reduced to 9N laterally. Further, the base module 634 may facilitate a connection with the user interface 622 to provide an alert to the doctor, at step 1312. In one embodiment, the base module 634 may facilitate connection with the user interface 622 to provide alerts to the doctor related to the ongoing surgery. In another embodiment, the base module 634 may inform the doctor about the new rules and safety regulations updated in the $3^{rd}$ party operating room equipment system database 636, so that during the intervention, the doctor should already be informed about the new rules and safety regulations of the surgery.

In one alternate embodiment, the surgical procedure may be fully autonomous by the surgical robot 602, without the interference of the $3^{rd}$ party operating room equipment system 628. In another embodiment, the surgical procedure may be fully manual by the doctor using the robot arm 606. In another embodiment, the surgical procedure may be a hybrid surgical procedure where few parts are controlled by the robot arm 606 and other parts are completed by the $3^{rd}$ party operating room equipment system 628 or where the robot arm 606 operates in a semiautonomous mode where the surgeon acts as a check to the robot arm 606, where the $3^{rd}$ party operating room equipment system 628 utilizing the data from the sensors 610 proposes an action, and the action is approved by the surgeon before the robot arm 606 executes the action. In one embodiment, during the hybrid surgical procedure, the robot arm 606 may handover some part of the procedure to the $3^{rd}$ party operating room equipment system 628, when sensitive areas require a doctor to manually control and then the $3^{rd}$ party operating room equipment system 628 may pass the control back to the robot arm 606 in an autonomous mode.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as disclosed above.

The functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

Some embodiments of this disclosure, illustrating all its features, will now be discussed in detail. The words "com-prising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

We claim:

1. A computer-implemented method for edge computing, the method comprising:
   establishing at least one communication channel between a surgical robot and a surgical equipment database storing at least one operational parameter for at least one surgical tool;
   performing, by the surgical robot, at least a portion of a surgical procedure using the at least one surgical tool;
   determining that the at least one operational parameter of the at least one surgical tool meets a threshold for the at least one surgical tool; and
   in response to determining that the at least one operational parameter meets the threshold:
   determining an action for the at least one surgical tool, and
   sending a signal to the at least one surgical tool and/or the surgical robot to perform the action.

2. The method of claim 1, wherein the surgical robot stores a plurality of machine-learning engines, each trained using a tool-specific training set for the at least one surgical tool, the method comprising:

monitoring operation of the at least one surgical tool using a corresponding machine-learning engine trained for the at least one surgical tool.

3. The method of claim 1, wherein the surgical robot stores at least one machine-learning engine trained with at least one training set for the at least one surgical tool, the method comprising:
receiving, by the at least one machine-learning engine, data associated with the at least one surgical tool; and
determining that a trigger event has occurred based on the data.

4. The method of claim 3, wherein the at least one training set comprises threshold values and trigger event threshold values for the at least one surgical tool.

5. The method of claim 3, wherein the action is performed on a patient, and wherein the at least one training set comprises historical data from patients that match the patient.

6. The method of claim 1, comprising:
analyzing, using edge computing by the surgical robot, data from the at least one surgical tool to monitor the at least one operational parameter, a surgical site, or a patient condition.

7. The method of claim 1, comprising:
analyzing, using edge computing by the surgical robot, data from at least one sensor to monitor the action, a surgical site of the patient, or a patient condition.

8. A non-transitory computer-readable medium storing instructions that, when executed by a computing system, cause the computing system to:
establish at least one communication channel between a surgical robot and a surgical equipment database storing at least one operational parameter for at least one surgical tool;
perform, by the surgical robot, at least a portion of a surgical procedure using the at least one surgical tool;
determine that the at least one operational parameter of the at least one surgical tool meets a threshold for the at least one surgical tool; and
in response to determining that the at least one operational parameter meets the threshold:
determine an action for the at least one surgical tool, and
send a signal to the at least one surgical tool and/or the surgical robot to perform the action.

9. The non-transitory computer-readable medium of claim 8, wherein the surgical robot stores a plurality of machine-learning engines, each trained using a tool-specific training set for the at least one surgical tool, and the instructions cause the computing system to:
monitor operation of the at least one surgical tool using a corresponding machine-learning engine trained for the at least one surgical tool.

10. The non-transitory computer-readable medium of claim 8, wherein the surgical robot stores at least one machine-learning engine trained with at least one training set for the at least one surgical tool, and the instructions cause the computing system to:
receive, by the at least one machine-learning engine, data associated with the at least one surgical tool; and
determine that a trigger event has occurred based on the data.

11. The non-transitory computer-readable medium of claim 10, wherein the at least one training set comprises threshold values and trigger event threshold values for the at least one surgical tool.

12. The non-transitory computer-readable medium of claim 10, wherein the action is performed on a patient, and wherein the at least one training set comprises historical data from patients that match the patient.

13. The non-transitory computer-readable medium of claim 8, wherein the instructions cause the computing system to:
analyze, using edge computing by the surgical robot, data from the at least one surgical tool to monitor the at least one operational parameter, a surgical site, or a patient condition.

14. The non-transitory computer-readable medium of claim 8, wherein the instructions cause the computing system to:
analyze, using edge computing by the surgical robot, data from at least one sensor to monitor the action, a surgical site of the patient, or a patient condition.

15. A system comprising:
one or more processors; and
one or more non-transitory memories storing instructions that, when executed by the one or more processors, cause the system to:
establish at least one communication channel between a surgical robot and a surgical equipment database storing at least one operational parameter for at least one surgical tool;
perform, by the surgical robot, at least a portion of a surgical procedure using the at least one surgical tool;
determine that the at least one operational parameter of the at least one surgical tool meets a threshold for the at least one surgical tool; and
in response to determining that the at least one operational parameter meets the threshold:
determine an action for the at least one surgical tool, and
send a signal to the at least one surgical tool and/or the surgical robot to perform the action.

16. The system according to claim 15, wherein the surgical robot stores a plurality of machine-learning engines, each trained using a tool-specific training set for the at least one surgical tool, and the instructions cause the system to:
monitor operation of the at least one surgical tool using a corresponding machine-learning engine trained for the at least one surgical tool.

17. The system according to claim 15, wherein the surgical robot stores at least one machine-learning engine trained with at least one training set for the at least one surgical tool, and the instructions cause the system to:
receive, by the at least one machine-learning engine, data associated with the at least one surgical tool; and
determine that a trigger event has occurred based on the data.

18. The system according to claim 17, wherein the at least one training set comprises threshold values and trigger event threshold values for the at least one surgical tool.

19. The system according to claim 17, wherein the action is performed on a patient, and wherein the at least one training set comprises historical data from patients that match the patient.

20. The system according to claim 15, wherein the instructions cause the system to:
analyze, using edge computing by the surgical robot, data from the at least one surgical tool to monitor the at least one operational parameter, a surgical site, or a patient condition.

* * * * *